US012097116B2

(12) United States Patent
Lee

(10) Patent No.: US 12,097,116 B2
(45) Date of Patent: *Sep. 24, 2024

(54) PROSTHETIC HEART VALVE FOR MULTIPLE POSITIONS AND ASSEMBLING METHOD THEREOF

(71) Applicant: SEVEN SUMMITS MEDICAL, Inc., Casper, WY (US)

(72) Inventor: Albert Yuheng Lee, Rancho Santa Margarita, CA (US)

(73) Assignee: SEVEN SUMMITS MEDICAL, INC, Casper, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/202,267

(22) Filed: May 25, 2023

(65) Prior Publication Data

US 2023/0414347 A1 Dec. 28, 2023

Related U.S. Application Data

(63) Continuation of application No. 17/852,349, filed on Jun. 28, 2022, now Pat. No. 11,701,224.

(51) Int. Cl.
*A61F 2/24* (2006.01)
*A61F 2/00* (2006.01)

(52) U.S. Cl.
CPC .......... *A61F 2/2418* (2013.01); *A61F 2/0077* (2013.01); *A61F 2250/001* (2013.01)

(58) Field of Classification Search
CPC ........ A61F 2/24; A61F 2/2409; A61F 2/2418; A61F 2/07; A61F 2/82
See application file for complete search history.

(56) References Cited

U.S. PATENT DOCUMENTS

| | | | | |
|---|---|---|---|---|
| 4,680,031 A | * | 7/1987 | Alonso | A61F 2/2412 623/2.13 |
| 4,705,516 A | * | 11/1987 | Barone | A61F 2/2409 623/2.39 |
| 4,725,274 A | * | 2/1988 | Lane | A61F 2/2412 623/2.18 |
| 4,851,000 A | * | 7/1989 | Gupta | A61F 2/2418 623/2.18 |
| 6,454,799 B1 | * | 9/2002 | Schreck | A61F 2/2433 623/2.14 |

(Continued)

OTHER PUBLICATIONS

Written Opinion of the International Searching Authority,PCT/US23/69265, Maile Date Dec. 12, 2023.

*Primary Examiner* — Seema Mathew
(74) *Attorney, Agent, or Firm* — Treasure IP Group, LLC

(57) ABSTRACT

Disclosed is a prosthetic heart valve and an assembling method thereof. The prosthetic heart valve comprises a universal core which can be universally used in different implantation positions and different application scenarios, and an adapter selected from more than one adapters which are respectively suitable for the different application scenarios. The universal core has a plurality of cantilever struts softly connected by a wire to form a supporting structure for a leaflet structure. The prosthetic heart valve according to the present disclosure has better flexibility and wider application range compared with various existing prosthetic heart valves, and may save time cost and research and development cost.

24 Claims, 20 Drawing Sheets

(56) References Cited

U.S. PATENT DOCUMENTS

| | | | | |
|---|---|---|---|---|
| 7,717,955 B2* | 5/2010 | Lane | ............... | A61F 2/2418 |
| | | | | 623/2.14 |
| 7,803,186 B1* | 9/2010 | Li | ............... | A61F 2/2418 |
| | | | | 623/2.18 |
| 9,241,790 B2* | 1/2016 | Lane | ............... | A61F 2/2412 |
| 9,308,087 B2* | 4/2016 | Lane | ............... | A61F 2/2436 |
| 9,579,193 B2* | 2/2017 | Rafiee | ............... | A61F 2/2418 |
| 9,655,719 B2* | 5/2017 | Board | ............... | A61F 2/2418 |
| 9,763,657 B2* | 9/2017 | Hacohen | ............... | A61F 2/2436 |
| 9,855,141 B2* | 1/2018 | Dienno | ............... | A61F 2/2418 |
| 10,010,417 B2* | 7/2018 | Keidar | ............... | A61F 2/2433 |
| 11,633,278 B2* | 4/2023 | Noe | ............... | A61F 2/2445 |
| | | | | 623/1.14 |
| 11,701,224 B1* | 7/2023 | Lee | ............... | A61F 2/0077 |
| | | | | 623/2.17 |
| 11,931,256 B1* | 3/2024 | Tan | ............... | A61F 2/2418 |
| 2004/0236411 A1* | 11/2004 | Sarac | ............... | A61L 27/3641 |
| | | | | 623/2.14 |
| 2004/0254627 A1* | 12/2004 | Thompson | ............... | A61F 2/915 |
| | | | | 623/1.11 |
| 2006/0052867 A1* | 3/2006 | Revuelta | ............... | A61F 2/2409 |
| | | | | 623/2.38 |
| 2006/0259137 A1* | 11/2006 | Artof | ............... | A61F 2/243 |
| | | | | 623/2.11 |
| 2007/0260305 A1* | 11/2007 | Drews | ............... | A61F 2/243 |
| | | | | 623/2.11 |
| 2008/0215144 A1* | 9/2008 | Ryan | ............... | A61F 2/2418 |
| | | | | 623/2.18 |
| 2009/0157175 A1* | 6/2009 | Benichou | ............... | A61F 2/2415 |
| | | | | 623/2.18 |
| 2010/0211165 A1* | 8/2010 | Schreck | ............... | A61F 2/2469 |
| | | | | 623/2.18 |
| 2010/0298931 A1* | 11/2010 | Quadri | ............... | A61F 2/243 |
| | | | | 623/2.11 |
| 2011/0166636 A1* | 7/2011 | Rowe | ............... | A61F 2/2433 |
| | | | | 623/1.26 |
| 2012/0022640 A1* | 1/2012 | Gross | ............... | A61F 2/2427 |
| | | | | 623/2.11 |
| 2012/0065729 A1* | 3/2012 | Pintor | ............... | A61F 2/2409 |
| | | | | 623/2.14 |
| 2013/0190862 A1* | 7/2013 | Pintor | ............... | A61F 2/2403 |
| | | | | 623/2.18 |
| 2013/0218267 A1* | 8/2013 | Braido | ............... | A61F 2/2433 |
| | | | | 623/2.18 |
| 2015/0359631 A1* | 12/2015 | Sheahan | ............... | A61F 2/2418 |
| | | | | 623/2.19 |
| 2016/0030169 A1* | 2/2016 | Shahriari | ............... | A61F 2/2418 |
| | | | | 623/2.18 |
| 2016/0045165 A1* | 2/2016 | Braido | ............... | A61F 2/2412 |
| | | | | 623/2.1 |
| 2016/0045316 A1* | 2/2016 | Braido | ............... | A61B 5/6847 |
| | | | | 623/2.38 |
| 2016/0074161 A1* | 3/2016 | Bennett | ............... | A61F 2/2412 |
| | | | | 29/890.126 |
| 2016/0296331 A1* | 10/2016 | Chung | ............... | A61F 2/2409 |
| 2016/0302918 A1* | 10/2016 | Keidar | ............... | A61F 2/2418 |
| 2019/0209304 A1* | 7/2019 | Lee | ............... | A61F 2/2475 |
| 2019/0388221 A1* | 12/2019 | Lee | ............... | A61F 2/2412 |
| 2021/0205078 A1* | 7/2021 | Carlino | ............... | A61F 2/2418 |
| 2022/0151779 A1* | 5/2022 | Pintor | ............... | A61F 2/2427 |
| 2022/0287830 A1* | 9/2022 | Peckels | ............... | A61F 2/2415 |
| 2023/0146082 A1* | 5/2023 | Dasi | ............... | A61L 27/20 |
| | | | | 623/2.17 |
| 2024/0148497 A1* | 5/2024 | Bukin | ............... | A61F 2/2436 |

\* cited by examiner

PROSTHETIC HEART VALVE FOR MULTIPLE POSITIONS AND ASSEMBLING METHOD THEREOF

FIELD OF THE DISCLOSURE

The present disclosure relates to a technical field of medical devices, in particular to a prosthetic heart valve which can be applied to a plurality of application scenarios, and an assembling method of a prosthetic heart valve.

DESCRIPTION OF THE RELATED ART

Native heart valves, such as aortic, pulmonary, mitral, and tricuspid valves, serve critical functions in assuring the forward flow of an adequate supply of blood through the cardiovascular system. These heart valves can be rendered less effective by congenital, inflammatory, or infectious conditions. Such damage to the valves can result in serious cardiovascular compromise or even death, thus it may be eventually necessary to replace a native heart valve with a prosthetic heart valve by surgery or minimally invasive transcatheter implantation.

At present, there are many known structures of prosthetic heart valves, such as a prosthetic aortic valve for surgical implantation, a prosthetic aortic valve for transcatheter aortic valve implantation (TAVI), and so on. These existing structures of the prosthetic heart valves are specifically developed per position and per application and cannot be universally suitable in various application scenarios. For example, a prosthetic aortic valve developed for surgical implantation may not be used for transcatheter implantation, and a prosthetic pulmonary valve cannot be implanted as a prosthetic mitral valve.

Due to ever tightening regulatory requirements, it takes nearly 10 years to put a newly developed prosthetic heart valve into the market, thus research and development cost and time cost required to develop prosthetic heart valve products for different application scenarios are high. Therefore, it is expected to provide a prosthetic heart valve that, to a certain extent, can be universally adaptable to various application scenarios.

SUMMARY OF THE INVENTION

In view of this, an objective of the present disclosure is to provide a prosthetic heart valve comprising a universal core which can be universally used in different implantation positions and different application scenarios, and an adapter selected from more than one adapters which are respectively suitable for the different application scenarios. The prosthetic heart valve according to the present disclosure has a better flexibility and adaptability for a broad variety of end use applications, compared to various existing prosthetic heart valves, and may save time and research and development expenditure.

According to one aspect of the present disclosure, there is provided a prosthetic heart valve. The prosthetic heart valve comprises:

a universal core, adaptable for different application scenarios, comprised of
  a ring-shaped stent, having a distal end and a proximal end in an axial direction, and comprising: a mesh structure as a circumferential sidewall, which allows the stent to be contracted or expanded in a radial direction, wherein the stent is configured to have blood flow from the proximal end to the distal end; and a plurality of cantilever struts, having various length, each of which extends distally from the proximal end of the mesh structure;
  a leaflet structure, comprising a plurality of leaflets, each of which is attached to the stent and at least has a portion disposed within the stent, wherein the leaflet structure allows blood to flow from the proximal end to the distal end through the prosthetic heart valve and inhibits blood flowing from the distal end to proximal end through the prosthetic heart valve;
  a designated adapter, which is selected from more than one adapters suitable for the different application scenarios and configured to anchoring the stent at a target position, wherein the stent and any one of the more than one adapters are detachably connected with each other based on the plurality of cantilever struts,
wherein the plurality of cantilever struts, which are softly connected by a wire to form a supporting structure for the leaflet structure, are each configured to move in at least three degrees of freedom.

In some embodiments, each one of the plurality of leaflets has an arc constraint edge for being secured with the sent, and a free edge which is disposed within the stent, wherein the free edge allows blood flowing from the proximal end to the distal end through the prosthetic heart valve when being separated from any other one of the plurality of leaflets, and inhibits blood flowing from the distal end to the proximal end through the prosthetic heart valve when being in contact with any other one of the plurality of leaflets, wherein at least a portion of the arc constraint edge is folded out from an interior of the stent to an outer circumferential surface of the stent based on the wire and the plurality of cantilever struts, so as to make the arc constraint edge wrap over the wire and the proximal end of the stent.

In some embodiments, the arc constraint edge of each one of the plurality of leaflets has a lower edge portion at the proximal end and opposing side edge portions, each of the edge portions is secured with an adjacent side edge portion of another one of the plurality of leaflets to form a commissure, wherein the free edge extends between the side edge portions of the arc constraint edge, and the proximal end of the stent has a contour matched with a lower contour shaped by the lower edge portions of the plurality of leaflets.

In some embodiments, the mesh structure comprises a plurality of first mesh cells and a plurality of second mesh cells distributed in a circumferential direction, the plurality of leaflets are each attached to a corresponding one of the plurality of second mesh cells or a corresponding one of the plurality of cantilever struts, and are independent with the adapter.

In some embodiments, the prosthetic heart valve further comprises a first covering layer covering at least a portion of an inner side of the stent and having a skirt-like shape, wherein the first covering layer comprises: a first portion, which is sutured with the plurality of second mesh cells, and is at least partially sandwiched between the plurality of leaflets and the plurality of second mesh cells; and/or a second portion, which matches the proximal end of the stent in location and shape, and is sutured with a corresponding portion of the stent.

In some embodiments, an edge, at the distal end, of the first covering layer has a contour matched with several frames of the mesh structure, wherein the several frames comprise: a distal-end frame of one or more of mesh cells comprising of the plurality of second mesh cells and the first mesh cells adjacent to each of the plurality of second mesh cells; a proximal-end frame of one or more of the plurality of first mesh cells other than the first mesh cells adjacent to each of the plurality of second mesh cells; a rod frame, which is shared by adjacent first mesh cells, of one or more of the first mesh cells adjacent to each of the plurality of second mesh cells.

In some embodiments, the first covering layer at least fully covers the plurality of second mesh cells, the first mesh cells adjacent to each of the plurality of second mesh cells, and the plurality of cantilever struts, and/or at least one of the plurality of first mesh cells is partially exposed by the first covering layer.

In some embodiments, the prosthetic heart valve further comprises a second covering layer covering an outer side of the stent and having a skirt-like shape, wherein the second covering layer comprises: a first portion, which is sutured together with the plurality of second mesh cells and the first portion of the first covering layer; and/or a second portion, which has a proximal-end contour matching the proximal end of the stent in location and shape, and is sutured together with a corresponding portion of the stent and the second portion of the first covering layer.

In some embodiments, an edge, at the distal end, of the second covering layer has a contour matched with a distal-end frame of one or more of the plurality of second mesh cells.

In some embodiments, the first covering layer and the second covering layer are integrated as a one-piece covering layer, which wraps over the proximal end of the stent based on the wire and the plurality of cantilever struts and is at least partially sandwiched between the stent and the plurality of leaflets at the proximal end; or the first covering layer and the second covering layer are separated covering layers.

In some embodiments, the prosthetic heart valve further comprises a base covering layer, which encloses an inner circumferential surface and/or an outer circumferential surface of the adapter, so as to prevent blood flow from flowing through a direction other than a direction between a proximal-end opening and a distal-end opening of the adapter.

In some embodiments, the base covering layer is sutured to one or both of the first covering layer and the second covering layer.

In some embodiments, the at least a portion of the arc constraint edge of each one of the plurality of leaflets is sewn along a certain distance from an edge, at the proximal end of the stent, to a position on the outer circumferential surface of the stent.

In some embodiments, the plurality of cantilever struts each have a cavity arranged at the proximal end, and the cavities of the plurality of cantilever struts are softly connected by the wire and are selected from holes, slots, and slits; and/or material of the wire may be metal or suture, or other suitable material.

According to another aspect of the present disclosure, there is provided an assembling method of the prosthetic heart valve in accordance with embodiments of the present disclosure, and the assembling method comprises: softly connecting the plurality of cantilever struts by the wire; connecting each one of the plurality of leaflets together with the stent based on the wire and the plurality of cantilever struts by sewing; and selecting and connecting the designated adapter with the plurality of cantilever struts by sewing.

In some embodiments, each one of the plurality of leaflets has an arc constraint edge and a free edge which is disposed within the stent, the free edge allows blood flowing from the proximal end to the distal end through the prosthetic heart valve when being separated from any other one of the plurality of leaflets, and inhibits blood flowing from the distal end to the proximal end through the prosthetic heart valve when being in contact with any other one of the plurality of leaflets, wherein step of connecting each one of the plurality of leaflets together with the stent based on the wire and the plurality of cantilever struts by sewing comprises: folding at least a portion of the arc constraint edge of each one the plurality of leaflets out from an interior of the stent to an outer circumferential surface of the stent based on the wire and the plurality of cantilever struts, so as to make the arc constraint edge wrap over the wire and the proximal end of the stent; and suturing the at least a portion of the arc constraint edge together with the proximal end of the stent.

In some embodiments, the mesh structure comprises a plurality of first mesh cells and a plurality of second mesh cells distributed in a circumferential direction, the plurality of leaflets are each attached to a corresponding one of the plurality of second mesh cells and/or a corresponding one of the plurality of cantilever struts, and are independent with the adapter.

In some embodiments, the prosthetic heart valve further comprises a first covering layer covering at least a portion of an inner side of the stent and having a skirt-like shape, wherein the assembling method further comprises: suturing a first portion of the first covering layer with the plurality of second mesh cells, so as to allow the first portion of the first covering layer being at least partially sandwiched between the plurality of leaflets and the plurality of second mesh cells; and/or suturing a second portion of the first covering layer with a corresponding portion of the stent, wherein the second portion of the first covering layer matches the proximal end of the stent in location and shape.

In some embodiments, the prosthetic heart valve further comprises a second covering layer covering an outer side of the stent and having a skirt-like shape, wherein the assembling method further comprises: suturing a first portion of the second covering layer together with the plurality of second mesh cells and the first portion of the first covering layer; and/or suturing a second portion of the second covering layer together with a corresponding portion of the stent and the second portion of the first covering layer, wherein the second portion of the second covering layer matches the proximal end of the stent in location and shape.

In some embodiments, the assembling method further comprises: providing a one-piece covering layer by laser cut as an integrated covering layer including the first covering layer and the second covering layer, wherein the one-piece covering layer wraps over the proximal end of the stent based on the wire and the plurality of cantilever struts, and is at least partially sandwiched between the stent and the plurality of leaflets at the proximal end; or providing the first covering layer and the second covering layer which are separated.

In some embodiments, the prosthetic heart valve further comprises a base covering layer, which encloses an inner circumferential surface and/or an outer circumferential surface of the adapter, so as to prevent blood flow from flowing through a direction other than a direction between a proximal-end opening and a distal-end opening of the adapter.

In some embodiments, the assembling method further comprises: suturing the base covering layer to one or both of the first covering layer and the second covering layer.

In some embodiments, the step of suturing the at least a portion of the arc constraint edge together with the proximal end of the stent comprises: suturing the at least a portion of the arc constraint edge of each one of the plurality of leaflets by sewing along a certain distance from an edge, at the proximal end of the stent, to a position on the outer circumferential surface of the stent.

In some embodiments, the assembling method further comprises: connecting a sewing ring to an outer surface of the designated adapter.

The prosthetic heart valve and the assembling method thereof provided according to the embodiments of the present disclosure is mainly formed by a universal core and an adapter which are structurally and functionally independent with each other, and are detachably connected via cantilever struts of the universal core. The universal core comprises a leaflet structure and an annular stent with the cantilever struts and a mesh structure, and is universally suitable for various application scenarios, for example, allows for stand-alone surgical or clamp down transcatheter valve delivery. The stent with mesh structure provides stability for the prosthetic heart valve, and the leaflets are attached to the cantilever struts and/or a distal-end portion of the stent. According to a designated application scenario, the adapter can be selected from more than one adapters, which are respectively adapting to various application scenarios, and is configured to anchor the universal core at a corresponding implantation position. Each cantilever strut is a flexible cantilever that is configured to move in at least three degrees of freedom and allows for slight deformations from various adaptors of various applications, thus will have minimal impact on the valve structure. Therefore, the prosthetic heart valve provided according to the embodiments of the present disclosure has good universality and flexibility, and can obviously save cost of time, research, and development, improve the utilization efficiency of the production line, and accelerate the procedure to put the prosthetic heart valve in clinical practice and market.

Further, the plurality of cantilever struts can be softly connected by a wire, so as to form a supporting structure for the leaflet structure, and help improve the longevity of the prosthetic heart valve.

In some optional embodiments, the cantilever struts may be provided with cavities, a connecting structure (e.g., suture or wire) may pass through those cavities to form a support structure for supporting the leaflet structure, such that each leaflet may be attached to the stent at the proximal end based on the cantilever struts. Those cavities can also be used to be connected to the designated adapter.

In some optional embodiments, the second mesh cells can be provided with a cantilever strut/cavity to further provide steadily support for the commissures and/or edges of the leaflets.

In some optional embodiments, each second mesh cell can be provided with a gap for receiving a corresponding one of the leaflets, thus each leaflet may have a continuous arcuate edge which can be folded from the inner space of the stent to the outer side of the stent without forming a slit, thus improving durability and material stability of the leaflet structure.

BRIEF DESCRIPTION OF THE DRAWINGS

The above and other objects, features and advantages of the present disclosure will become more apparent from the following description of embodiments of the present disclosure with reference to the accompanying drawings, in which.

DETAILED DESCRIPTION OF EMBODIMENTS OF THE DISCLOSURE

Figure 1:
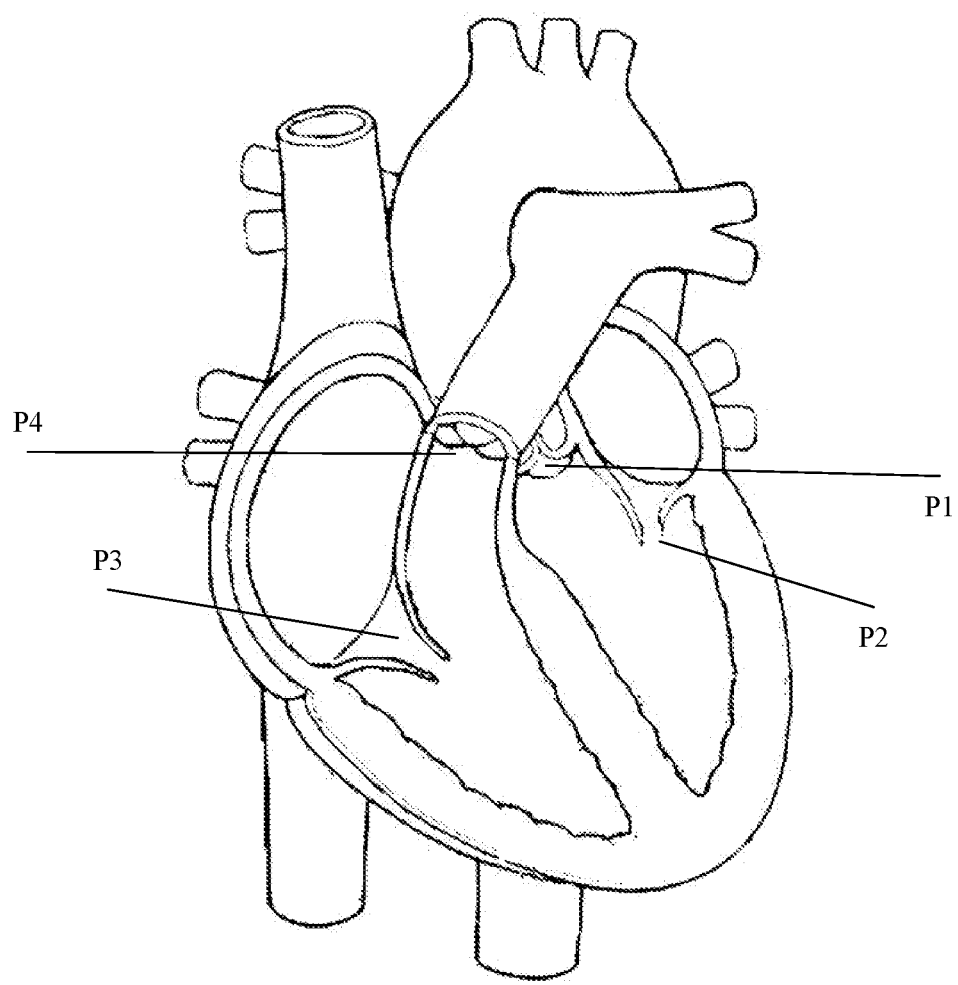
FIG. 1 is a cross section of a heart demonstrating positions of native valves.

The present disclosure will be described in more detail below with reference to the accompanying drawings. Throughout the various figures, like elements are denoted by like reference numerals. For the sake of clarity, various parts in the drawings are not drawn to scale. In addition, some well-known parts may not be shown in the figure.

Several exemplary embodiments of prosthetic heart valves are disclosed herein and shown in the attached figures. These embodiments should not be construed as limiting in any way. Instead, the present disclosure is directed toward all novel and nonobvious features and aspects of the various disclosed embodiments, alone and in various combinations and sub-combinations with one another.

Application Scenarios

FIG. 1 is a cross section of a heart demonstrating positions of native valves.

As shown in FIG. 1, a healthy heart is four-chambered and comprises a left atrium, a right atrium, a left ventricle, and a right ventricle. The left and right sides of the heart are separated by a wall generally referred to as a septum. The native valves of the heart include: a mitral valve P2 for connecting the left atrium to the left ventricle, an aortic valve P1 for connecting the left ventricle to the aorta, a tricuspid valve P3 for connecting the right atrium to the right ventricle, and a pulmonary valve P4 for connecting the right ventricle to the pulmonary artery.

If a native valve is diseased, the prosthetic heart valve can be implanted into the diseased position by surgery or transcatheter implantation, so as to replace that natural valve with the prosthetic heart valve.

Traditional prosthetic heart valves are usually developed for a single application scenario, thus may only be suitable for a single implantation position (aortic valve position, mitral valve position, tricuspid valve position or pulmonary valve position), a single implantation method/procedure (surgical implantation or transcatheter implantation) and a single implantation condition (stenosis or insufficiency, etc.). Therefore, medical device manufacturers need to develop various products according to different implantation positions, implantation methods and implantation conditions, which significantly increases the difficulty and cost for research and development, moreover, end-users also need to procure various prosthetic heart valves suitable for different application scenarios according to different needs.

According to the embodiments of the present disclosure, there is provided a prosthetic heart valve, wherein the prosthetic heart valve, or at least part of it, can be used as a universal prosthetic heart valve, or having a universal core, which is capable of being applied to various application scenarios without being changed, so that the cost and the time expenditure for research and development can be alleviated, the end users' product utilization efficiency can be improved, and the procedure to put the prosthetic heart valve in clinical practice can be accelerated.

In one variation, the prosthetic heart valve of the present invention is configured to be used in more than one target implantation positions, including but not limited to, aortic valve position, mitral valve position, tricuspid valve position or pulmonary valve position. In another variation, the prosthetic heart valve of the present invention is configured to be administered through one or more implantation procedures, including but not limited to, surgical implantation or transcatheter implantation. In still another variation, the prosthetic heart valve of the present invention is configured to be tailored to treat more than one conditions, including but not limited to, stenosis or insufficiency, etc.

Basic Structures

Figure 2:
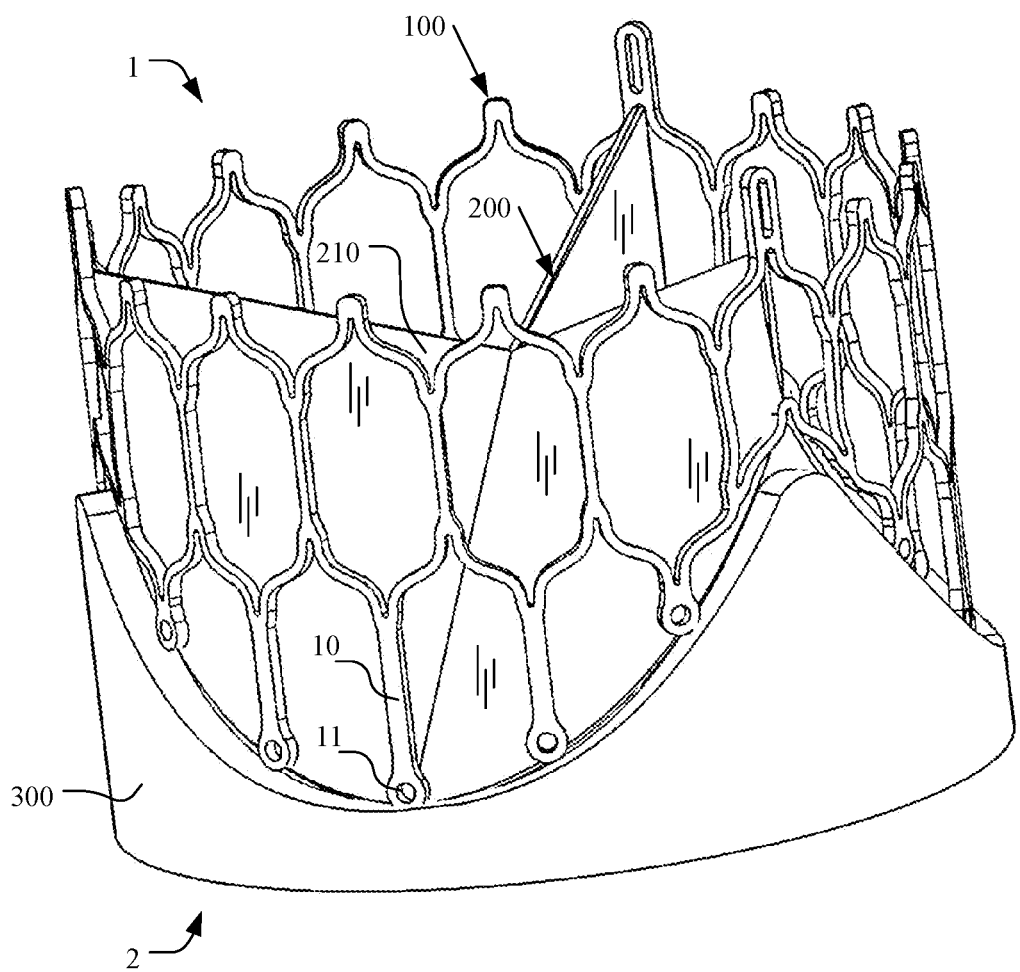
FIG. 2 shows a schematic structural diagram of a prosthetic heart valve according to an embodiment of the present disclosure.

FIG. 2 shows a schematic structural diagram of a prosthetic heart valve according to an embodiment of the present disclosure.

As shown in FIG. 2, the prosthetic heart valve 1000 mainly comprises a universal core and an adapter 300, which is functionally and structurally separated from the universal core. The universal core comprises a leaflet structure 200 that allows one-way flow of blood and the adapter 300 is used to anchor the prosthetic heart valve 1000 at a target implantation position.

The universal core according to the embodiments of the present disclosure can be universally adapted to a variety of application scenarios, which may correspond to different implantation positions (e.g., aortic valve position, pulmonary valve position, mitral valve position, tricuspid valve position), different implantation procedures (e.g., surgical or transcatheter implantation method) and/or different implantation conditions (e.g., stenosis, insufficiency, etc.).

As shown in FIG. 2, the universal core comprises a stent 100 and a leaflet structure 200 attached to the stent 100.

The stent 100 can be annular, and has a distal end 1 and a proximal end 2 opposite to each other in the axial direction, and a mesh structure as a circumferential sidewall of the stent 100, The mesh structure is configured to allow the stent 100 to collapse or expand along the radial direction. Based on the mesh structure, the stent 100 is able to radially expand from a collapsed state to an expanded state after being placed in a desired implantation position in the heart.

In some optional embodiments, material of the stent 100 can be medical stainless steel, nickel-titanium alloy (nitinol) or cobalt-chromium alloy, etc.

In some optional embodiments, a wall thickness along the radial direction of the stent 100 may be 0.1-1 mm, e.g., 0.2 mm-0.6 mm.

In some optional embodiments, a diameter of the stent 100 may be 5 mm to 55 mm, e.g, 10-30 mm, and the diameter can be the same or different from a diameter of the adapter 300. As an example, a diameter difference between the stent 100 and the adapter 300 can be 1-2 mm, according to material of the adapter 300.

The leaflet structure 200 comprises a plurality of leaflets 210, each of which at least has a portion disposed within stent 100. The leaflet structure 200 is configured to allow blood flow from the proximal end 2 to the distal end 1 through the prosthetic heart valve 1000 and inhibit blood flow from the distal end 1 to the proximal end 2 through prosthetic heart valve 1000. As an example, as shown in FIG. 2, the leaflet structure 200 may be formed by three leaflets 210 connected with each other, and each leaflet 210 is attached to a corresponding position of the stent 100.

In some optional embodiments, material of each leaflet 210 may be bovine pericardium, porcine pericardium or polymer material. In some optional embodiments, a wall thickness of each leaflet may be 0.1-0.7 mm, e.g., 0.2-0.45 mm.

In various embodiments of the present disclosure, the adapter 300 connected with the universal core may be a designated adapter selected from a plurality of adapters provided with different configurations (e.g. structures, sizes and/or materials). The plurality of adapters 300 are respectively adapting to different application scenarios, and are respectively provided with, for example, various adapter configurations suitable for different implantation positions (aortic valve, pulmonary valve, mitral valve, tricuspid valve, etc.), different implantation methods (e.g., surgical or transcatheter implantation method), and different implantation conditions (stenosis, insufficiency, etc.). Based on this, in practical applications, the prosthetic heart valve 1000 adapted to a required application scenario can be obtained only by selecting, according to the required application scenario, the designated adapter 300 from the plurality of adapters, without changing or replacing the universal core including the stent 100 and the leaflet structure 200.

That is to say, by combining an invariable universal core with different adapters 300, prosthetic heart valves 1000 adapted to various application scenarios can be simply obtained. As an example, an adapter 300 adapted to aortic valve position may be selected from the plurality of adapters to be connected with the universal core, thereby obtaining a prosthetic heart valve suitable for aortic valve implantation position; as another example, an adapter 300 adapted to transcatheter implantation method may be selected from the plurality of adapters to be connected with the universal core, thereby obtaining a prosthetic heart valve that can be implanted to a corresponding target position by transcatheter implantation method, and the like.

Specifically, a designated adapter 300 adapted to a requested application scenario may be detachably connected to the stent 100 for anchoring the stent 100 and the leaflet structure 200 attached to the stent 100 to a target position, so that native leaflets at the target position can be replaced by the leaflet structure 200.

In some implementations, each of the more than one adapters 300 may be annular and is capable of being connected to the stent 100 via a physical connection scheme supported by a plurality of cantilever struts 10. Each of the more than one adapters may have a blood flow-in end matching the proximal end 2 of the stent 100 in contour shape, so that the universal core is capable of being conformably fitted to different adapters 300. Said physical connection scheme includes but not limited to, linking connection between a wire and hole or slots assembly, insertion connections between a thread and slits, and other female/male joints.

Figure 3:
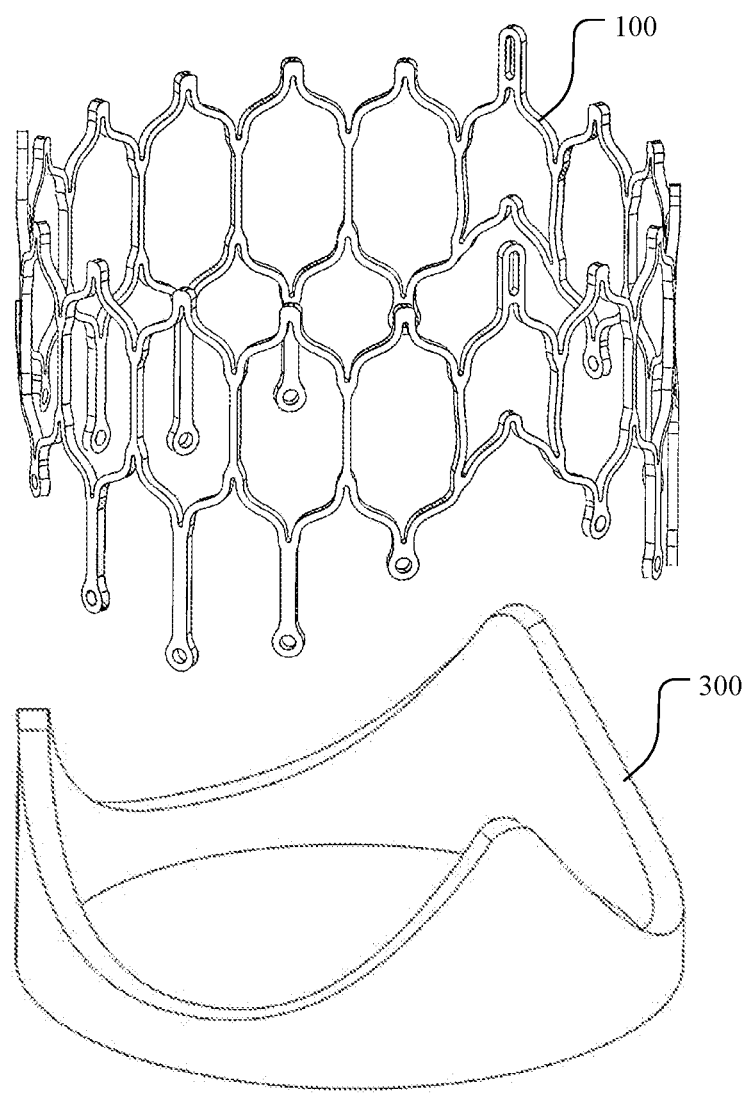
FIG. 3 and FIG. 4 respectively show schematic structural diagrams of two different adapters that can be selected for the prosthetic heart valve of an embodiment of the present disclosure.
Figure 4:
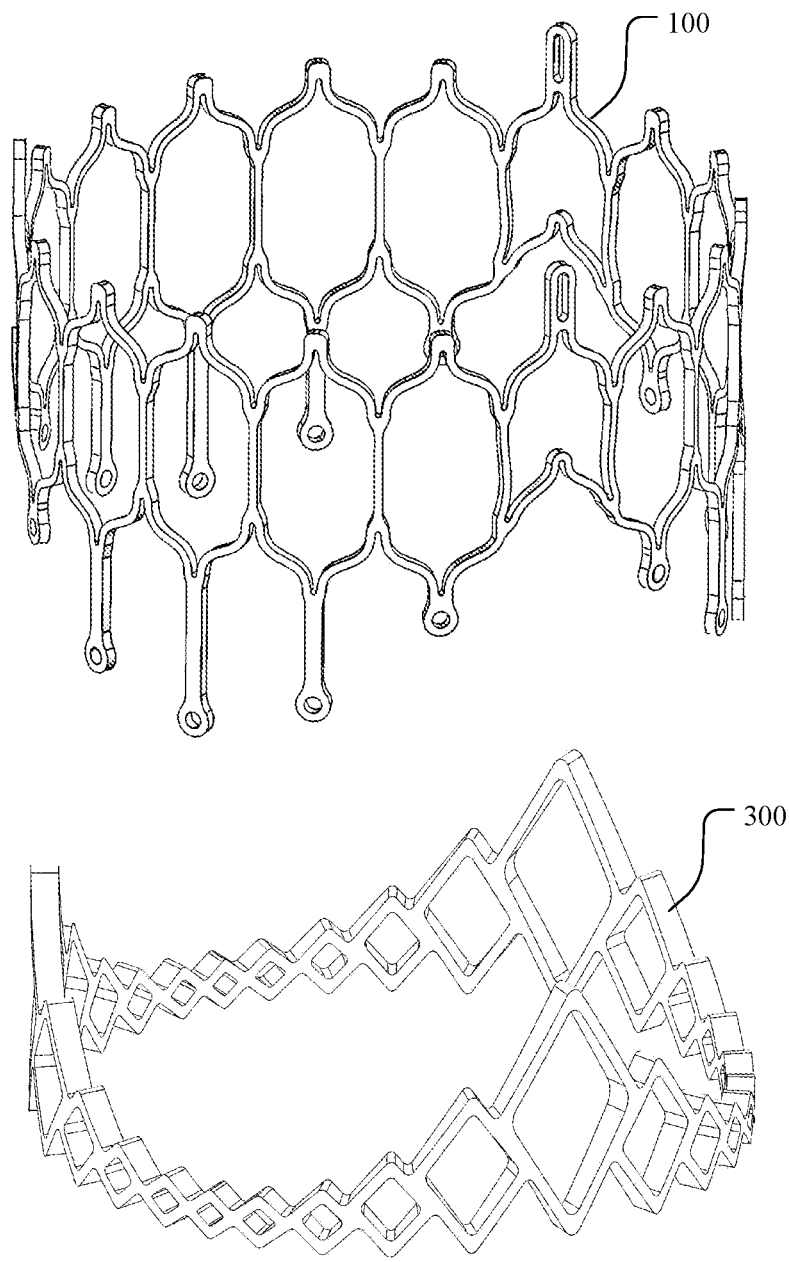

FIG. 3 and FIG. 4 respectively show schematic structural diagrams of two different adapters that can be selected for the prosthetic heart valve of an embodiment of the present disclosure. The adapters comprise a top surface and a bottom surface. The top surface is comprised of a continuous peak-valley contour, configured to conformally attach or couple with the stent. In the adapter of the present invention, a ratio between a peak height to valley height ranges from 20:1 to 1.2:1. Said peak height is a longest distance from the top surface to the bottom surface along the vertical direction; whereas the valley height is a shortest distance from the top surface to the bottom surface along the vertical direction.

The bottom surface of the adapter is configured to be secured to a target position through a second purity of connectors, including but not limited to a row of evenly distributed the cavities, for example, holes, slots and slits and a thread of wire and sutures.

The stent 100 has a height, which is a longest distance from the proximal end to the distal end. In the present invention, a ratio between the height of the stent 100 to the peak height of the adapter is from 20:1 to 1:1, inclusive. In one example, ratio between the height of the stent 100 to the peak height of the adapter is 10:1. In another example, ratio between the height of the stent 100 to the peak height of the adapter is 2:1. In another example, ratio between the height of the stent 100 to the peak height of the adapter is from 1.8:1. In still another example, ratio between the height of the stent 100 to the peak height of the adapter is from 1.5:1. In yet another example, ratio between the height of the stent 100 to the peak height of the adapter is from 1.2:1.

As shown in FIGS. 2 to 4, the adapter 300 may have a ring structure or a ring-like structure, so that the adapter 300 can be anchored at various implant locations.

As an example, the adapter 300 as shown in FIGS. 2 and 3 has a rigid or semi-rigid solid structure, so that it can be adapted to an implantation mode based on classical surgical implementations. The radial diameter of the adapter 300 is the same with a diameter of the stent 100 in at least one of its expanded state.

As another example, the adapter 300 as shown in FIG. 4 is made of a mesh structure or comprises a hollow structure that can be expanded or contracted in the radial direction, so that it can be adapted to an implantation mode based on expandable surgical implantation commutating future value-in-value procedure.

Various adapters 300 may be detachably connected to the stent 100 in various ways (e.g., stitching, hooking, embedding, etc.) at the proximal end 2 so that the adapters 300 of the prosthetic heart valve 1000 can be conveniently replaced according to the requested application scenario, without changing the universal core.

Figure 5:
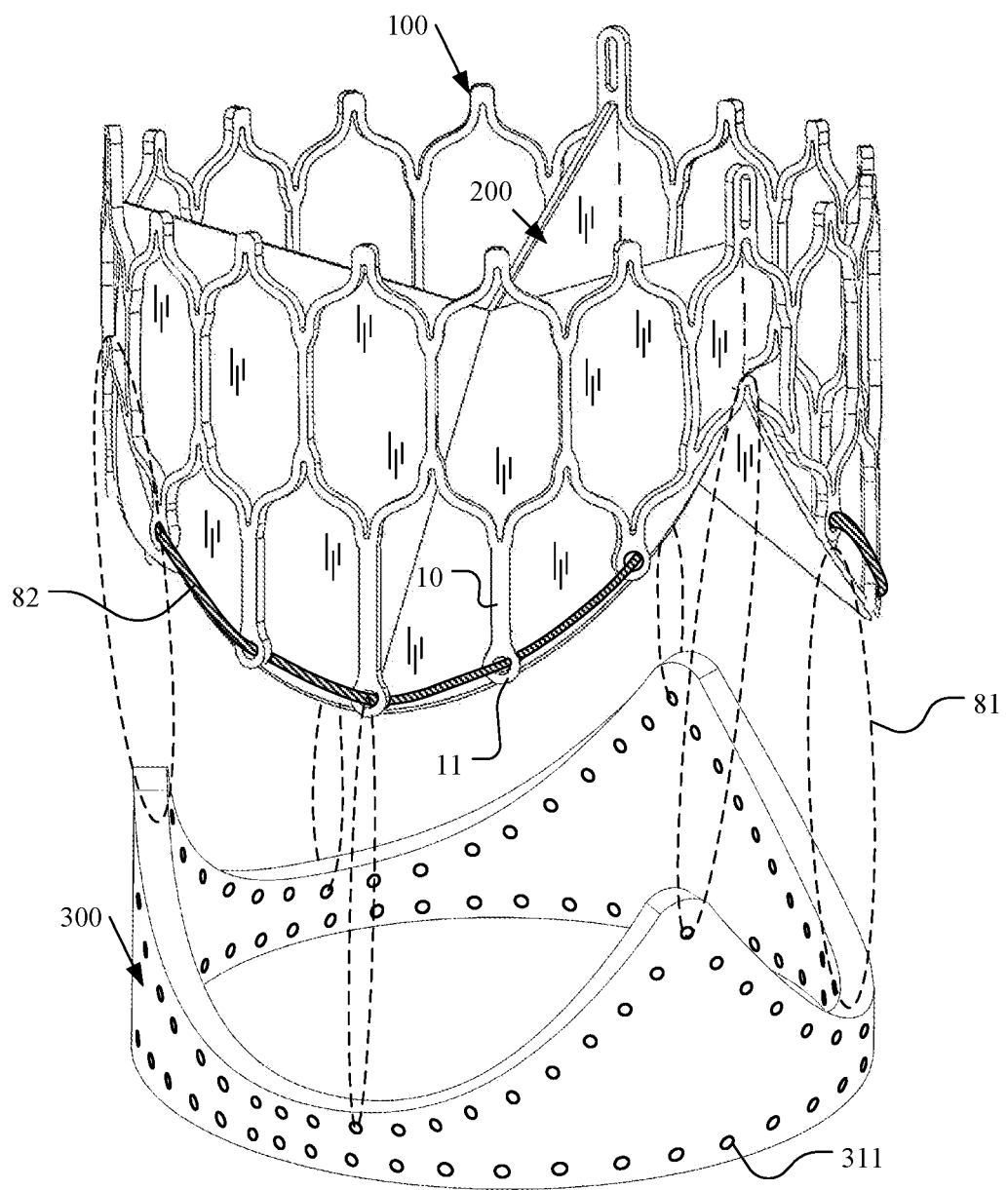
FIG. 5 shows a schematic structural diagram of a prosthetic heart valve according to an embodiment of the present disclosure.
Figure 6:
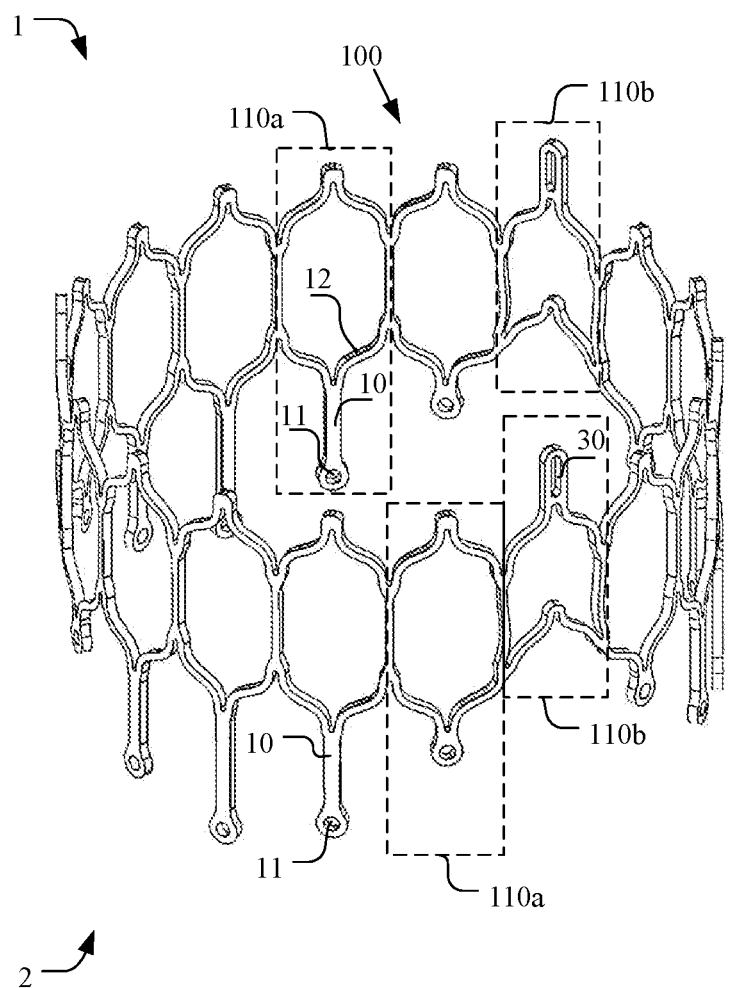
FIG. 6 shows a schematic structural diagram of an example of a stent according to an embodiment of the present disclosure.
Figure 7:
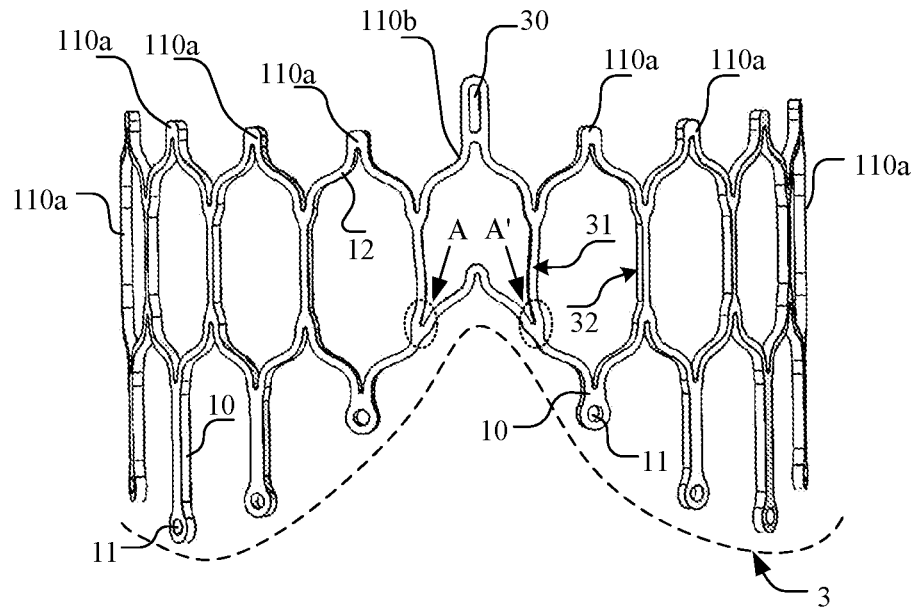
FIG. 7 shows a side view of the stent shown in FIG. 6.

FIG. 5 shows a schematic structural diagram of a prosthetic heart valve according to an embodiment of the present disclosure. For a sole purpose of clarity, the adapter 300 in FIG. 5 is drawn separately from the universal core compared to FIG. 2 and the dashed lines drawn in FIG. 5 are only used to exemplarily illustration the connecting structure (e.g., suture or wire) used for connecting the stent 100 and the adapter 300. Further, FIG. 6 shows a schematic structural diagram of an example of a stent according to an embodiment of the present disclosure, and FIG. 7 shows a side view of the stent shown in FIG. 6.

As an example, referring to shown FIGS. 2 to 6, the stent 100 comprises a mesh structure 110 and a plurality of cantilever struts 10 connected to the mesh structure 110. The adapter 300 can be detachably connected to the stent 100 based on the plurality of cantilever struts 10.

As an example, a width of each cantilever struts 20 may be 0.1-1 mm, e.g., 0.2 mm-0.7 mm.

Each of the cantilever struts 10 extends, for example, from the mesh structure to the proximal end 2 by a certain length, thereby serving as a flexible cantilever that may not affect the collapsing and expanding of the stent 100. As a cantilever, each cantilever strut 210 has a fixed end, which is permanently attached to the mesh structure, and a flexible end, extending to the proximal end 2, thus the plurality of cantilever struts 10, in one variation, each of the plurality of cantilever struts has at least three degrees of freedom of movement, including two translation movements and one rotation movement. The two translational movements are selected from three translation movements along x, y, and z axis directions, for example, x and y axis directions. The x, y, and z directions are defined in a coordinate where the connecting point between the mesh structure and fixed end of the cantilever strut as an origin. The rotational movement is selected from two rotation movements, a spin and a revolution. Spin is defined as a rotation around an axis of itself, to allow the strut cantilever end to rotate around itself. Revolution is defined as for the strut cantilever end to rotate around an axis of not itself, for example an axis of a cylinder shape of the mesh structure circumferential sidewall, or an axis or pseudo-axis formed when the strut cantilever end is lifted and wind around rotate. In another variation, each of the plurality of cantilever struts 10 can further translation along an additional direction, for example along the z axis. In still another variation, the each of the plurality of cantilever struts 10 can further rotate along an additional axis. The movement in three or four degrees of freedom allow for slight deformations from various adapters of various applications, and may have minimal impact on the structure of the prosthetic heart valve 1000. Since the flexible end of each cantilever strut 10 is flexible, it can be suitably connected to adapters 300 of various sizes and/or shapes without changing or replacing the structure of the stent 100.

As an example, at least one of the cantilever struts 10 may be slightly deformed (e.g., bended, twisted, and/or tilted based on the fixed end as a fulcrum), such that the flexible end of each of the cantilever struts 10 may deviated from its original position to a subsequent position to fit the corresponding adapter 300.

As an example, the mesh structure 110 and the plurality of cantilever struts 10 can be integrally formed of a same material. The material may have enough toughness to allow the mesh structure to collapse and expand, and allow the flexible end of each cantilever strut to have at least three degrees of freedom, including translations along x, y and z axis directions.

As an example, at least one of the cantilever struts 10 is provided with a cavity 11 for allowing various adapters 300 to be connected to the stent 100. For example, as shown in FIGS. 2 to 6, the cavity may be a hole disposed at the proximal end 2 of the stent 100. As an optional example, as shown in FIG. 5, the adapter 300 may be provided with cavities 311 corresponding to the cavities 11 positioned on the cantilever struts 10, such that the cantilever struts 10 may be detachably connected to the adapter 300 based on the cavities 11 and 311, for example, the stent 100 may be connected to the designated adapter 300 using a first connecting structure 82 (e.g., suture, wire, or other physical connecting structure) through the cavities 11 positioned on the cantilever struts 10 and the cavities 311 positioned on the adapter 300. The cavities 311 comprises at least two rows, a top row of cavities 311 is position along a top surface of the adapter 300 and a bottom row of cavities 311. The top rows of cavities 311 and cavities of the cantilever struts may form pairs to allow wires or sutures to connect them so that the universal core and adapter is connected. In one example, there are three sets of the cavities on the cantilever struts and cavities on the first row of adapters aligned vertically in proximity to form pairs.

The first connecting structure 82 (e.g., suture, wire, or other physical connecting structure) is mainly for supporting each leaflet, and helps improve the longevity of the prosthetic heart valve. Since the plurality of cantilever struts 10 are softly connected by the first connecting structure 82 to form a supporting structure for the leaflet structure, the first connecting structure 82 may be arranged to go through those cantilever struts without being too tight to deform each cantilever strut, or being too loose to fail to provide any support for the leaflet structure, and does not fix or tighten each cantilever strut in place, that is, each cantilever strut is not tightly sewn by the first connecting structure 82, so that those cantilever struts can still move in at least three degrees of freedom from blood pressure. At the same time, the covering(s) according to embodiments of the present disclosure may also be flexible enough to provide movement.

In some optional embodiments, a wire serving as the first connecting structure 82 may have a thickness ranging from 0.3 mm to 0.7 mm.

The density of the top row of cavities and bottom row of cavities may be the same and may not be the same for the purpose of the structural integrity. The bottom row of the cavities is configured to secure the adapter in a target location. In one example, the number of top row cavities 311 of the adapter is greater than the number of the cavities 11 of the stent 100. In another example, the number of top row cavities 311 of the adapter is less than the number of the cavities 11 of the stent 10. In one example there are 10 cavities on the top row. In another example there are 20 cavities on the top row.

In some embodiments, as shown in FIG. 5, a first connecting structure 82 (e.g., suture or wire) may pass through the hollow cavities 11 on each cantilever strut 10 to form a support structure for supporting the leaflet structure 200, such that each leaflet 210 of the leaflet structure 200 may be attached to the stent 100, at least based on a corresponding one of the cantilever struts 10.

In some embodiments, the first connecting structure 82 (e.g., suture or wire) may struck in cavities 11 on each cantilever strut 10 to form a support structure.

For example, an embodiment, each one of the plurality of leaflets 210 may have an arc constraint edge (shown as, for example, edge 27 in FIG. 9 or edge 25 in FIG. 21) for being secured with the sent 100, and a free edge (shown as, for example, edge 23 in FIG. 10) which is disposed within the stent, wherein the free edge allows blood flowing from the proximal end 2 to the distal end 1 through the prosthetic heart valve when being separated from any other one of the plurality of leaflets 210 in an open position, and inhibits blood flowing from the distal end 1 to the proximal end 2 through the prosthetic heart valve when being in contact with any other one of the plurality of leaflets 210 in a closed position. At least a portion of the arc constraint edge can be folded out from an interior of the stent 100 to an outer circumferential surface of the stent 100 based on the first connecting structure 82 (e.g., suture or wire) and the plurality of cantilever struts 10, so as to make the arc constraint edge wrap over the first connecting structure 82 (e.g., suture or wire) and the proximal end of the stent 100.

It should be noted that the cavities mentioned in the present disclosure are not limited to be the circular holes shown in FIGS. 2 to 6, but can also be designed as rectangle, oval, polygon, irregular shape or other shapes. In some alternative implementations, the cavities may also be implemented as slits and slots of various shapes as well. In some preferred embodiment, the slits may permit an easy insertion or penetration.

The mesh structure of the stent 100 comprises, for example, a plurality of first mesh cells 110*a* and a plurality of second mesh cells 110*b* distributed along the circumferential direction of the stent 100. The plurality of second mesh cells 110*b* respectively correspond to the commissures 20 formed by adjacent leaflets 210 in location, such that the commissures 20 can be secured to the stent 100 based on the second mesh cells 110b. The number of second mesh cells 110b may be greater than/equal to the number of leaflets 210.

In an implementation, as shown in FIG. 6, each of the first mesh cells 110a and each of the second mesh cells 110b may has a ring-like shape, and the first mesh cells 110a and the second mesh cells 110b are arranged sequentially along the circumferential direction of the stent 100 to form the sidewall of the stent 100. As an example, in order to facilitate collapsing and expanding, each first mesh cell 110a may has a shuttle-like shape with opposite ends pointing to the proximal and distal ends, respectively.

As an example, as shown in FIG. 7, each second mesh cell 110b has a first node A and a second node A' at the proximal end 2, which are the connection points of that second mesh cell 110b and the first mesh cells 110a adjacent to that second mesh cell 110b on opposite sides, respectively.

In some implementations, as shown in FIG. 7, two adjacent first mesh cells 110a may share a common edge 32, and each second mesh cell 110b and an adjacent one of the first mesh cells 110a may share a common edge 31 provided with the corresponding first node A or the corresponding second node A'.

As an example, as shown in FIGS. 6 and 7, each cantilever strut 10 may extend in the axial direction of the stent 100 between one end (close to the proximal end 2) of the corresponding first mesh cell 110a and the proximal end 2 of the stent 100, so as not to affect the collapsing and expanding of the stent 100.

In some implementations, every two adjacent second mesh cells 110b are spaced apart by at least one first mesh cell 110a. As an example, as shown in FIG. 6, the number of the first mesh cells 110a arranged between every two adjacent second mesh cells 110b may be constant. As a further example, the number of the first mesh cells 110a arranged between every two adjacent second mesh cells 110b may be odd, and/or, the lengths of the cantilever struts 10 of the first mesh cells 110a located between two adjacent second mesh cells 110b may sequentially decrease from the middle to both sides in the circumferential direction of the stent 100, such that the position of the flexible end of each cantilever strut 10 can be adapted to the position of the lower edge 22 of the corresponding leaflet 210 at the proximal end 2, which is beneficial for the cantilever struts 10 to provide support for the leaflets 210.

In some embodiments, as shown in FIGS. 6 and 7, at least one of the second mesh cells 110b may be provided with a connection cavity (e.g., hole, slit, or slot) 30 at the distal end 1, for being detachable connected to a delivery device for the prosthetic heart valve (e.g., by suture or wire). Each connection cavity 30 is not limited to the shape shown in the figures, but also can be designed in round, square, oval, polygon, irregular shape, etc.

Figure 8A:
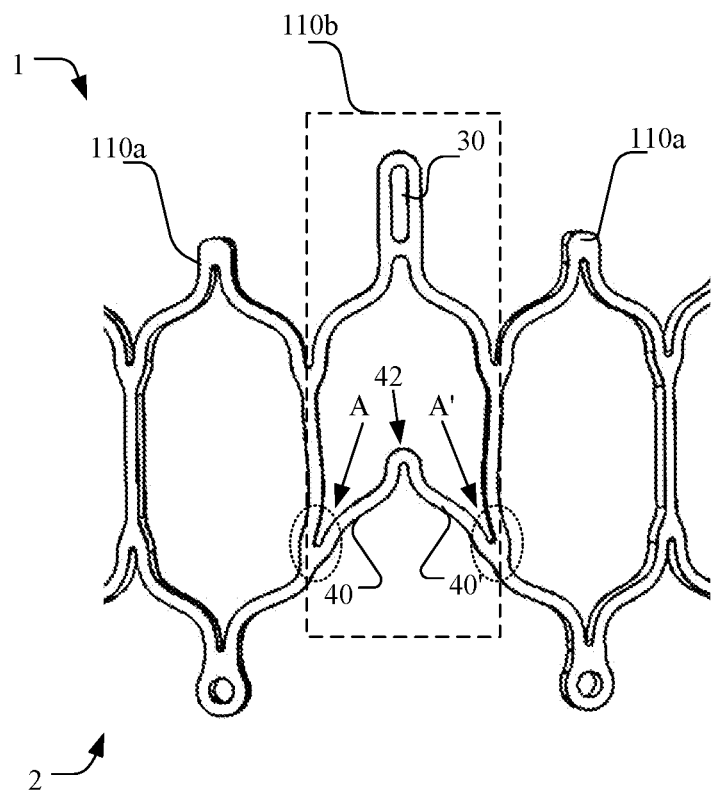
FIG. 8a shows a partial structural diagram of a first exemplary structure of a stent according to an embodiment of the present disclosure.

FIG. 8a shows a partial structural diagram of a first exemplary structure of a stent according to an embodiment of the present disclosure.

As shown in FIG. 8a, each second mesh cell 110b comprises a first edge 40 extending from the first connection point A to an interior of that second mesh cell 110b, and a second edge 40' extending from the second connection point A' to the interior of that second mesh cell 110b, and the first edge 40 and the second edge 40' are converged at a junction (42) inside that second mesh cell 110b. A contour 3 defined by the first edges 40, the second edges 40' and flexible ends of the cantilever struts 10 of the stent 100 may match the proximal-end contour of the leaflet structure 200, such that each leaflet 210 can be secured to the stent 100 based on the first edges 40, the second edges 40' and the cantilever struts 10.

As an example, the contour 3 at the proximal end 2 of the stent 100 is an arc contour matched with a lower contour shaped by the lower edges 22 of the plurality of leaflets 210.

As an example, the junction 42 may be in arc shape, sharp-angled shape, or other shape, which includes shapes not specifically described in the present disclosure.

Figure 8B:
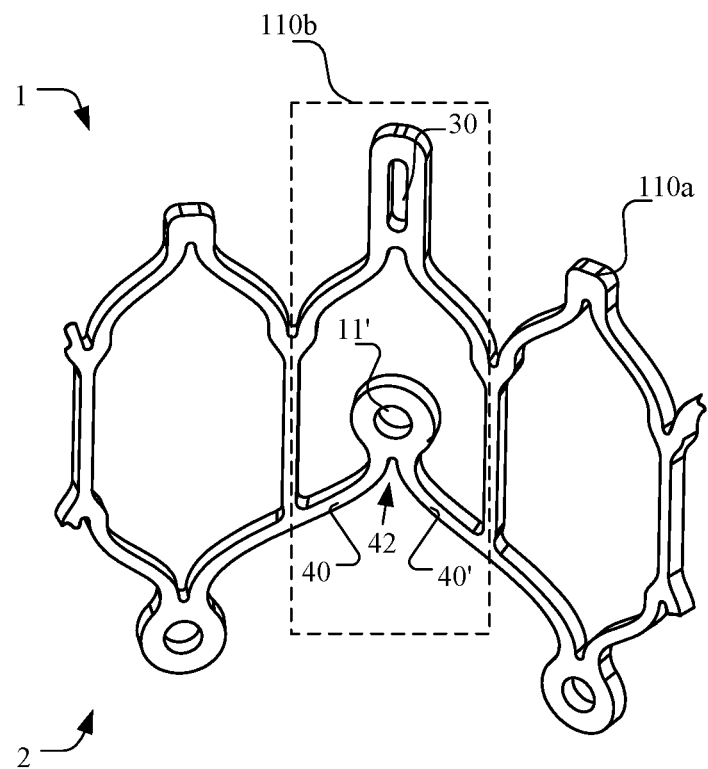
FIG. 8b shows a partial structural schematic diagram of a second exemplary structure of the stent according to an embodiment of the present disclosure.

FIG. 8b shows a partial structural schematic diagram of a second exemplary structure of the stent according to an embodiment of the present disclosure.

The second mesh cell 110b shown in FIG. 8b differs from the second mesh cell 110b shown in FIGS. 7 and 8a in that, in the second mesh cell 110b, the junction 42 of the first edge 40 and the second edge 40' may also be provided with a cavity 11', which can be used to connect with the cavities 11, which are fixed with the first mesh cells 110a, by suture or wire, thereby providing further support for the leaflet structure 200 at the proximal end 2.

Figure 8C:
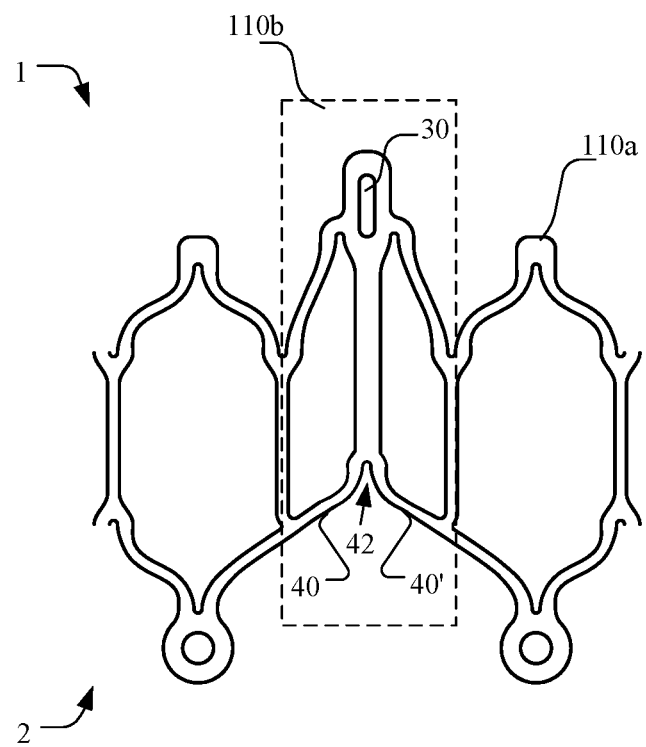
FIG. 8c shows a partial structural schematic diagram of a third exemplary structure of the stent according to an embodiment of the present disclosure.

FIG. 8c shows a partial structural schematic diagram of a third exemplary structure of the stent according to an embodiment of the present disclosure.

In some optional embodiments, the second mesh cell 110b shown in FIG. 8c differs from the second mesh cell 110b shown in FIGS. 7 and 8a in that, in the second mesh cell 110b, the first edge 40 and the second edge 40' may extend in a strut shape from the junction 42 to a top portion of that second mesh cell 110b at the distal end 1, thereby providing further support for the leaflet structure 200 at the distal end 1.

It should be noted that the stent 100 according to an embodiment of the present disclosure may include one or more exemplary structures of the second mesh cells provided by the above-mentioned examples referring to FIGS. 8a to 8c.

Figure 9:
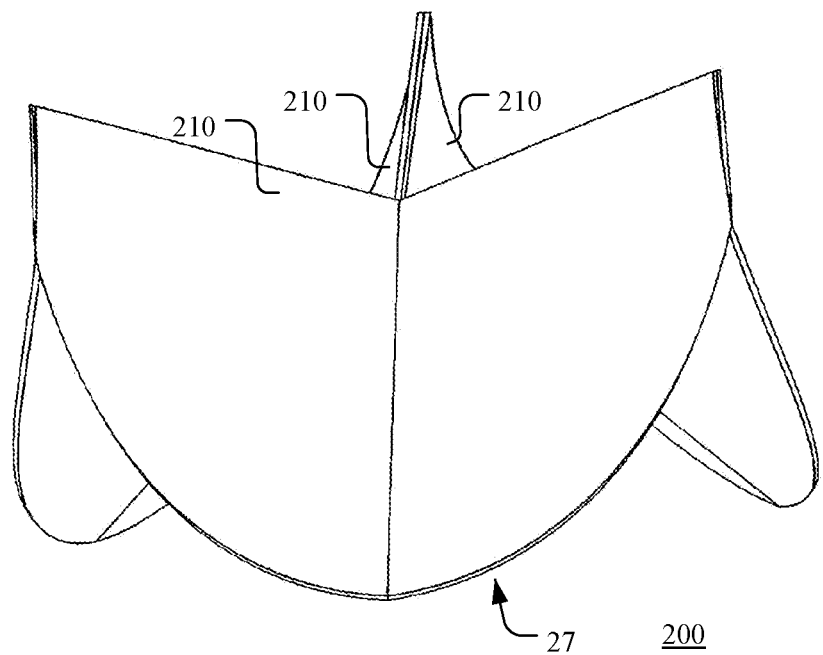
FIG. 9 shows a schematic diagram of a leaflet structure of an embodiment of the present disclosure.
Figure 10:
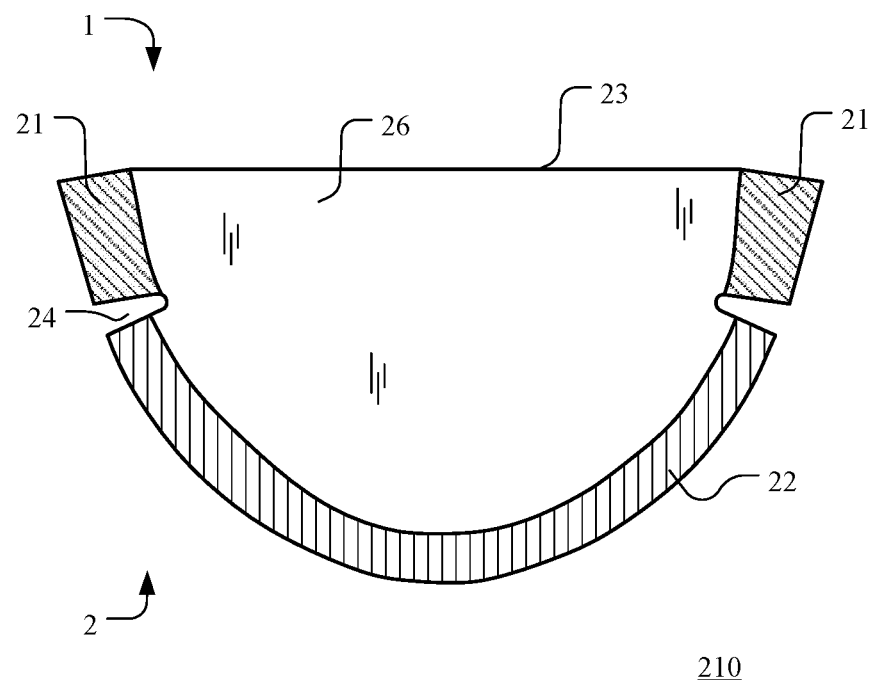
FIG. 10 shows a flattened view of a structure of a single leaflet according to an embodiment of the present disclosure.
Figure 11:
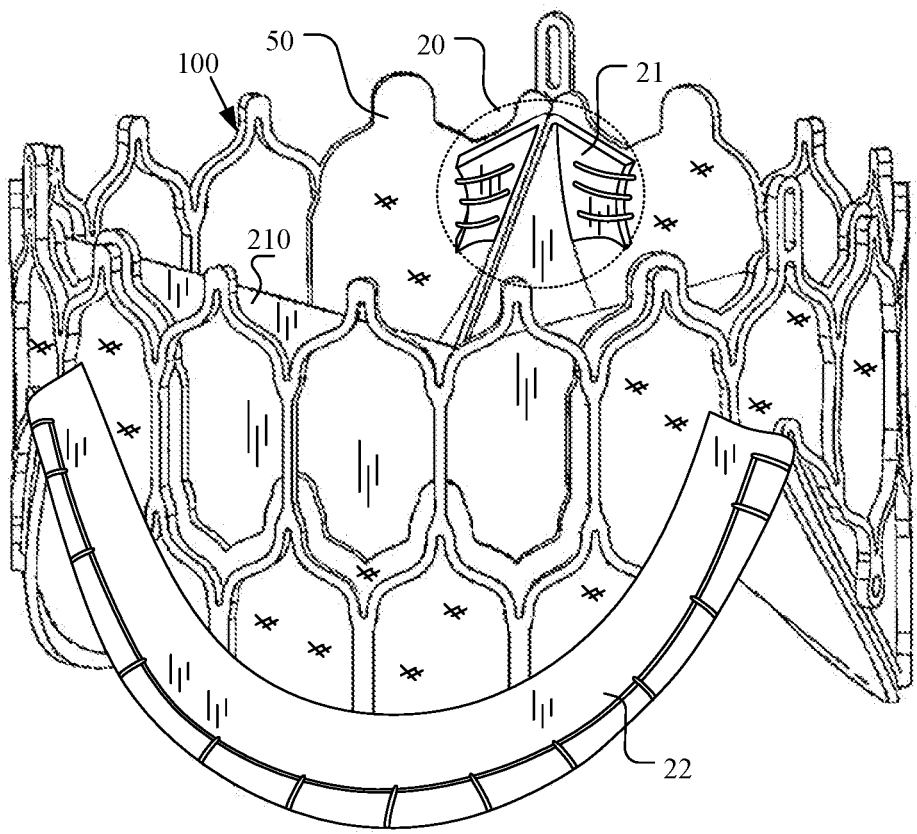
FIG. 11 shows a schematic structural diagram of an example of the universal core according to an embodiment of the present disclosure.

FIG. 9 shows a schematic diagram of a leaflet structure of an embodiment of the present disclosure. FIG. 10 shows a flattened view of a structure of a single leaflet according to an embodiment of the present disclosure. FIG. 11 shows a schematic structural diagram of an example of the universal core according to an embodiment of the present disclosure.

As shown in FIGS. 9 and 11, the leaflet structure 200 comprises a plurality of leaflets 210, configured to allow blood to flow from the proximal end 2 to the distal end 1 through the prosthetic heart valve 1000 and inhibit blood flowing from the distal end 1 to proximal end 2 through the prosthetic heart valve 1000. As part of the universal core, the leaflet structure 200 are independent with the adapter 300.

As a typical example, as shown in FIGS. 9 and 11, the leaflet structure 200 comprises three angled and interconnected leaflets 210, and the present disclosure is mainly illustrated by this example. However, the present disclosure does not limit the number of leaflets 210 in the leaflet structure 200, and the leaflet structure 200 may also consist of two or more than three leaflets 210.

As shown in FIG. 10, a flattened shape of one single leaflet 210 is, for example, semicircular or similar to a semicircular shape, each leaflet 210 has opposing side edges 21 at the distal end 1, an upper edge 23 (free edge) extending between its side edges 21, and a lower edge 22 at the proximal end 2, wherein each of the side edges 21 is secured with an adjacent side edge 21 of another leaflet 210 to form a commissure 20, so that adjacent leaflets 210 can be connected with each other at the commissure 20, as shown in FIG. 11. The commissures 20 formed by the plurality of leaflets 210 are attached to a top portion of the stent 100, as an example, the commissures 20 formed by the plurality of leaflets 210 can be attached to the plurality of second mesh cells 110b, respectively.

At least a portion of each leaflet 210 is disposed inside the stent 100. For example, as shown in FIG. 11, each commissure 20 can be positioned inside the stent 100 and attached to an inner side of a corresponding second mesh cell 110b, and the side edges 21 and the upper edges 23 of the plurality of leaflets 210 are disposed inside an inner space surrounded by the stent 100.

Figure 12:
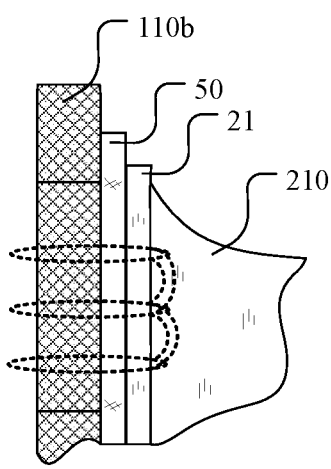
FIG. 12 shows a cross-sectional structure diagram of a portion of the universal core at a position of one of the commissures as shown in FIG. 11 along the radial direction of the stent.

The lower edges 22 of each leaflet 210 can be attached to the proximal end 2 of the stent 100, for example, the lower edges 22 can be attached to and supported by the cantilever struts 10 of the stent 100, as shown in FIG. 12. The lower edge 22 of one of the leaflets 210 is shown in FIG. 12, in light of this, although the lower edges of other leaflets 210 are not shown in the figures, it should be understood that they may also have a same configuration as the lower edge 22 shown in FIG. 12.

As an example, as shown in FIG. 11, the lower edge 22 of each leaflet 210 can be folded from the inner space surrounded by the stent 100 to an outer side of the stent 100 based on one or more of the cantilever struts 10, so that the lower edges 22 of the leaflets can be attached to the cantilever struts 10, for example, by suturing through the cavities 11 (e.g., holes, slots, and slits) arranged on the cantilever struts 10.

Based on any one of the exemplary stent structures referring to FIGS. 8a to 8c, for each leaflet 210, there is provide a slit 24 between the lower edge 22 and each of the side edges 21, the slit 24 may correspond to the junction 42 in location, so as to allow the lower edge 22 of that leaflet 210 to be folded from the inner side to the outer side of the stent 100 based on a curved contour (formed by the cantilever struts 10, the first edge 40 and the second edge 40' of a corresponding second mesh cell 110b) at the proximal end 2 of the stent 100, and at the same time, allow the side edges 21 to be attached to the opposite side (i.e., inner side) of the stent 100.

Further, the folded lower edges 22 of the plurality of leaflets 210 may also be attached to a corresponding portion of the stent 100 at the proximal end 2. The corresponding portion of the stent 100, for example, comprises one or more cantilever struts 10 of the stent 100.

In order to stably secure the leaflet structure 200 to the stent 100, one or more covering layers may be used.

Figure 13:
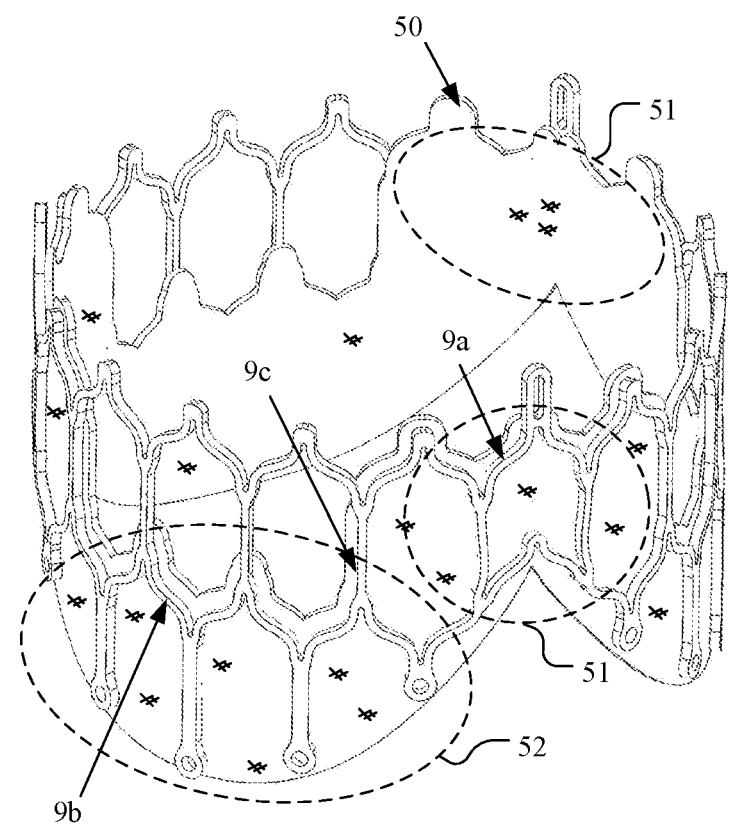
FIG. 13 shows a position relation between a first covering layer and the stent according to an embodiment of the present disclosure.
Figure 14:
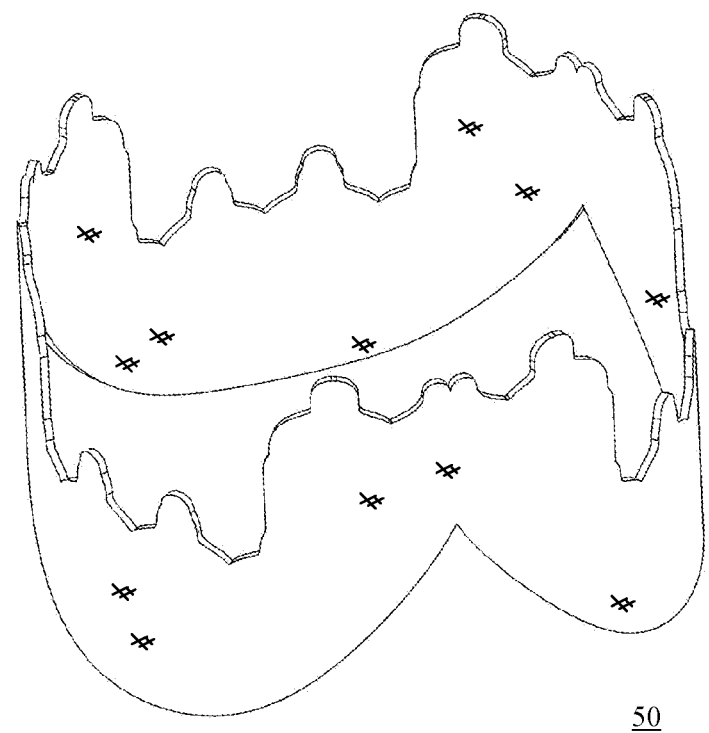
FIG. 14 shows a structure of the first covering layer as shown in FIG. 13.

FIG. 12 shows a cross-sectional structure diagram of a portion of the universal core at a position of one of the commissures as shown in FIG. 11 along the radial direction of the stent. FIG. 13 shows a position relation between a first covering layer and the stent according to an embodiment of the present disclosure. FIG. 14 shows a structure of the first covering layer as shown in FIG. 13.

In some optional embodiments, a first covering layer 50 is provided as a base for stitching, in order to secure the leaflets 210 to the stent 100. The first covering layer may have a skirt-like shape, as shown in FIGS. 11-14. It may cover at least a portion of the inner side of the stent 100, for example, fully or partially cover the plurality of second mesh cells 110b, the first mesh cells 110a adjacent to each of the plurality of second mesh cells, and the plurality of cantilever struts 10.

In some optional embodiments, as shown in FIGS. 11 and 13, at least one of the plurality of first mesh cells 110a is partially exposed by the first covering layer 50, so as to improve hemodynamic properties. In some other embodiments, all of the plurality of first mesh cells may be exposed by the first covering layer 50.

In some optional embodiments, as shown in FIGS. 12 and 13, the first covering layer 50 may comprise a first portion 51, which is at least partially sandwiched between the plurality of leaflets 210 and the plurality of second mesh cells 110b, so that the commissures 20 and/or the side edges 21 of the plurality of leaflets 210 can be secured to the plurality of second mesh cells 110b by applying blanket, locking and/or other type of stitching through the first portion 51 of the first covering layer 50.

In some optional embodiments, the first covering layer 50 may further comprise a second portion 52, which matches the lower edges 22 of the plurality of leaflets 210 in location and shape, so that the lower edges 22 of the plurality of leaflets 210 can be secured with the corresponding portion of the stent 100 by applying blanket, locking and/or other type of stitching through the second portion 52 of the first covering layer 50.

As an example, an edge, at the distal end, of the first covering layer 50 may have a contour matched with several frames of the mesh structure. For example, as shown in FIG. 13, the several frames may comprise: a distal-end frame 9a of one or more of mesh cells comprising of the plurality of second mesh cells and the first mesh cells adjacent to each of the plurality of second mesh cells; a proximal-end frame 9b of one or more of the plurality of first mesh cells other than the first mesh cells adjacent to each of the plurality of second mesh cells; a rod frame 9c, which is shared by adjacent first mesh cells, of one or more of the first mesh cells adjacent to each of the plurality of second mesh cells.

In some optional embodiments, the first covering layer 50 may at least fully cover the plurality of second mesh cells, a portion of the first mesh cells adjacent to each of the plurality of second mesh cells, and a portion (e.g., flexible end) of the plurality of cantilever struts 10. In some optional embodiments, at least a portion of an interval space between two adjacent ones of the plurality of cantilever struts are exposed by the first covering layer 50.

Figure 15:
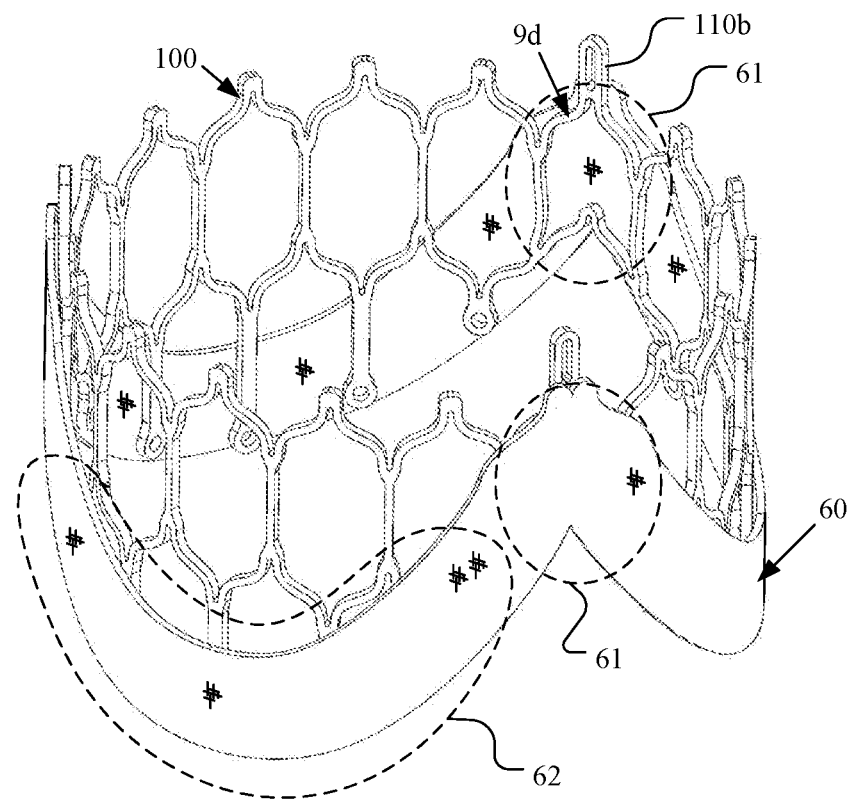
FIG. 15 shows a position relation between a second covering layer and the stent according to an embodiment of the present disclosure.
Figure 16:
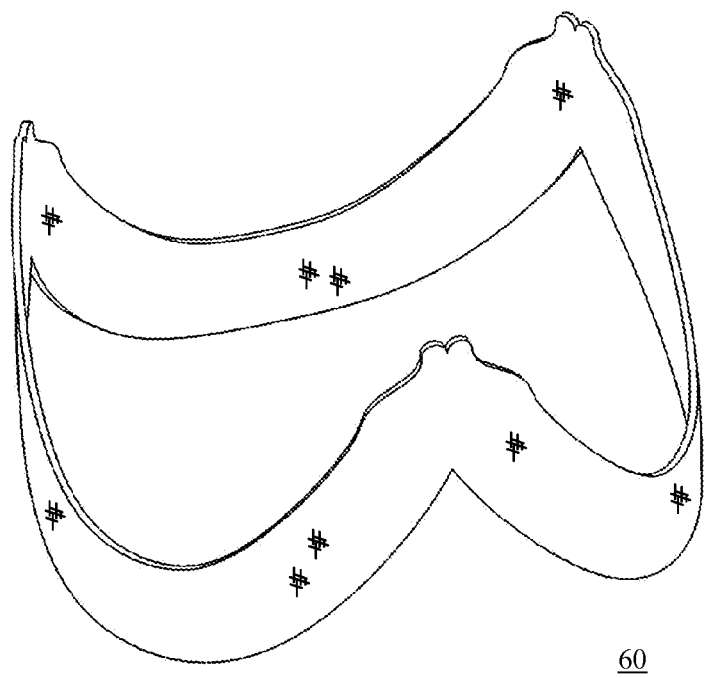
FIG. 16 shows a structure of the second covering layer as shown in FIG. 15.
Figure 17:
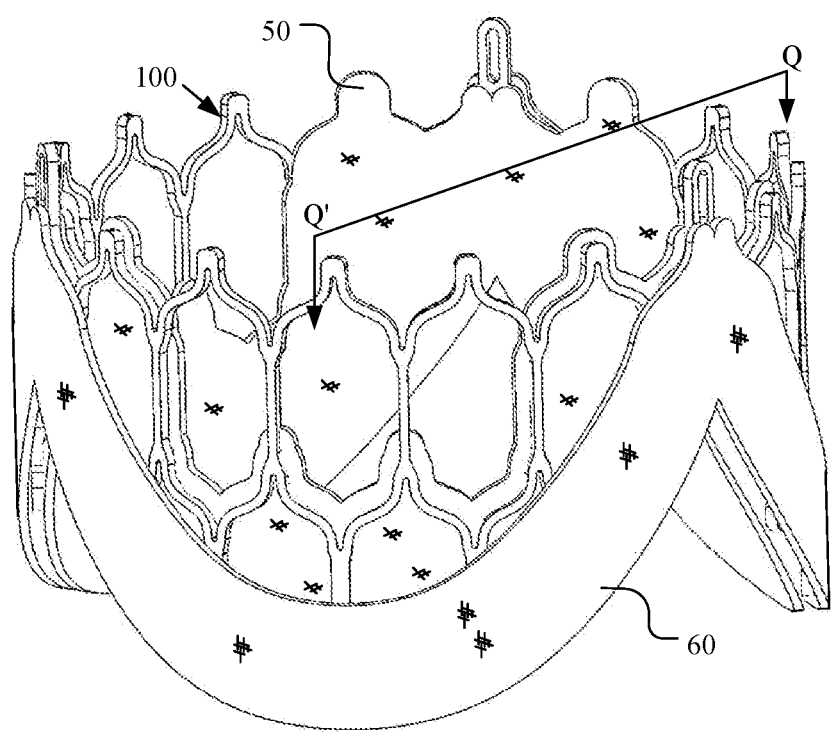
FIG. 17 shows a structural diagram of the stent with the first covering layer and the second covering layer according to an embodiment of the present disclosure.

FIG. 15 shows a position relation between a second covering layer and the stent according to an embodiment of the present disclosure, FIG. 16 shows a structure of the second covering layer as shown in FIG. 15, and FIG. 17 shows a structural diagram of the stent with the first covering layer and the second covering layer according to an embodiment of the present disclosure.

In some optional embodiments, a second covering layer 60 is further provided as a base for stitching, in order to secure the leaflets 210 to the stent 100.

The second covering layer 60 may have a skirt-like shape, as shown in FIGS. 15-17. It may cover at least a portion of the outer side of the stent 100, for example, fully or partially cover the plurality of second mesh cells 110b and the plurality of cantilever struts 10. In some optional embodiments, at least a portion of an interval space between two adjacent ones of the plurality of cantilever struts 10 are exposed by the first covering layer 50 and the second covering layer 60.

In some optional embodiments, as shown in FIGS. 15 and 17, at least one of the plurality of first mesh cells 110a is partially exposed by the second covering layer 60, so as to ensure hemodynamic properties. In some other embodiments, all of the plurality of first mesh cells may be exposed by the first covering layer 50.

In some optional embodiments, as shown in FIGS. 15 and 17, the second covering layer 60 may comprise a first portion 61, which is at least secured with the plurality of second mesh cells 110b, the first portion of the first covering layer and/or the side edges 21 of the plurality of leaflets 210, by applying blanket, locking and/or other type of stitching through the first portion 61 of the second covering layer 60.

In some optional embodiments, the second covering layer 60 may further comprise a second portion 62, which has a proximal-end contour matching the lower edges 22 of the plurality of leaflets 210 in location and shape, so that the lower edges 22 of the plurality of leaflets 210 can be secured with the corresponding portion of the stent 100 by applying blanket, locking and/or other type of stitching through the second portion 62 of the second covering layer 60. As an example, the second portion 62 of the second covering layer 60 can be sutured together with the corresponding portion of the stent 100 and the second portion 52 of the first covering layer 50.

In some optional embodiments, an edge, at the distal end, of the second covering layer 60 may have a contour matched with a distal-end frame 9d of one or more of the plurality of second mesh cells.

In some optional embodiments, the first covering layer 50 and the second covering layer 60 may be integrated as a one-piece covering layer, which wraps over the proximal end of the stent 100 based on the first connecting structure 82 and the plurality of cantilever struts 10, and may be at least partially sandwiched between the stent 100 and the plurality of leaflets 210 at the proximal end. Or, in some other embodiments, the first covering layer 50 and the second covering layer 60 may be separated covering layers with above-mentioned structural features.

In some optional embodiments, material of the first covering layer 50 and/or the second covering layer 60 can be PET or other material which promotes endothelialization. In some optional embodiments, thickness of the first covering layer 50 and/or the second covering layer 60 may be 0.05-0.5 mm, e.g., 0.1-0.25 mm.

It should be understood that the height of the second covering layer 60 may be changed based on design requirements. For example, a height of the second covering layer 60 may be almost a length of a selected one of the plurality of cantilever struts 10, or a maximum/average length of the plurality of cantilever struts 10; or, the second covering layer 60 may have a height matching the shape of the first covering layer 50.

Figure 18A:
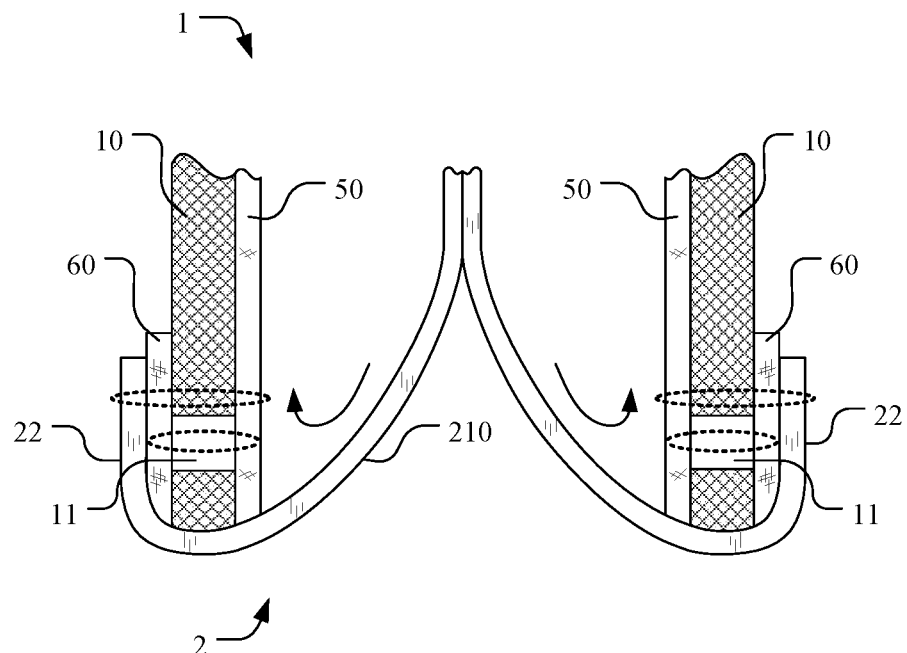
FIG. 18a shows a cross-section diagram of an implementation of the universal core along line QQ' shown in FIG. 17.
Figure 18B:
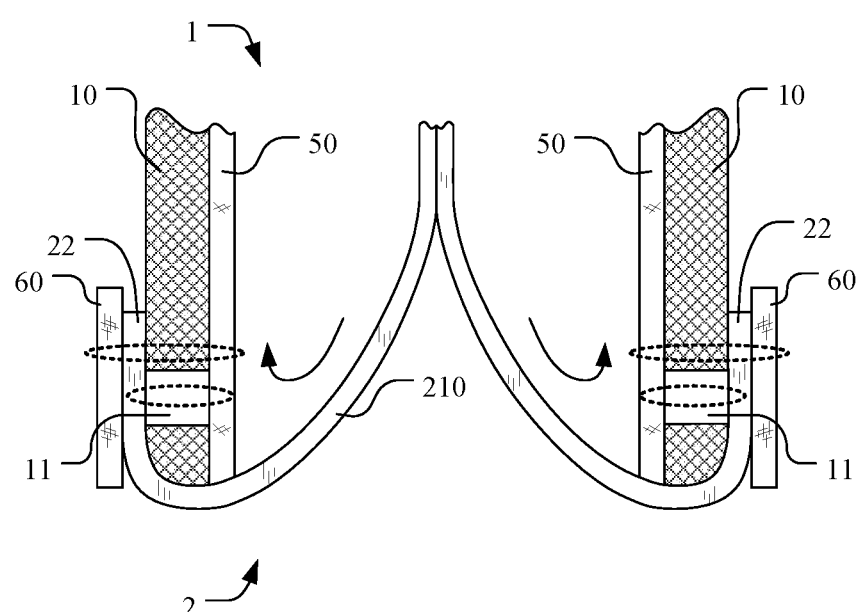
FIG. 18b shows a cross-section diagram of another implementation of the universal core along line QQ' shown in FIG. 17.

FIG. 18a shows a cross-section diagram of an implementation of the universal core along line QQ' shown in FIG. 17, and FIG. 18b shows a cross-section diagram of another implementation of the universal core along line QQ' shown in FIG. 17.

In an optional implementation, as shown in FIG. 18a, the second portion 62 of the second covering 60 is at least partially sandwiched between the corresponding portion of the stent 100 and the lower edges 22 that folded to the outer side of the stent 100 based on the first connecting structure 82 and the plurality of cantilever struts 10.

In an alternative implementation, as shown in FIG. 18b, the lower edges 22 that folded to the outer side of the stent 100 based on the first connecting structure 82 and the plurality of cantilever struts 10 are at least partially sandwiched between the second portion 62 of the second covering layer 60 and the corresponding portion of the stent 100.

In some embodiments, taking FIGS. 18a and 18b as examples, at least a portion, that is folded out from the interior of the stent 100 to an outer circumferential surface of the stent 100 based on the first connecting structure 82 and the plurality of cantilever struts 10, of the arc constraint edge of each leaflet can be sewn along a certain distance (e.g., 5 mm) from an edge, at the proximal end 2 of the stent 100, to a position on the outer circumferential surface of the stent 100. In some optional embodiments, as the wrapped-over portion of each leaflet 210 is mainly for supporting that leaflet and improving the longevity of the prosthetic heart, sewing points for each leaflet can be positioned at the edge, at the proximal end 2 of the stent 100, all the way to an end, which is wrapped over to the outer circumferential surface of the stent 100, of the arc constraint edge.

Figure 19:
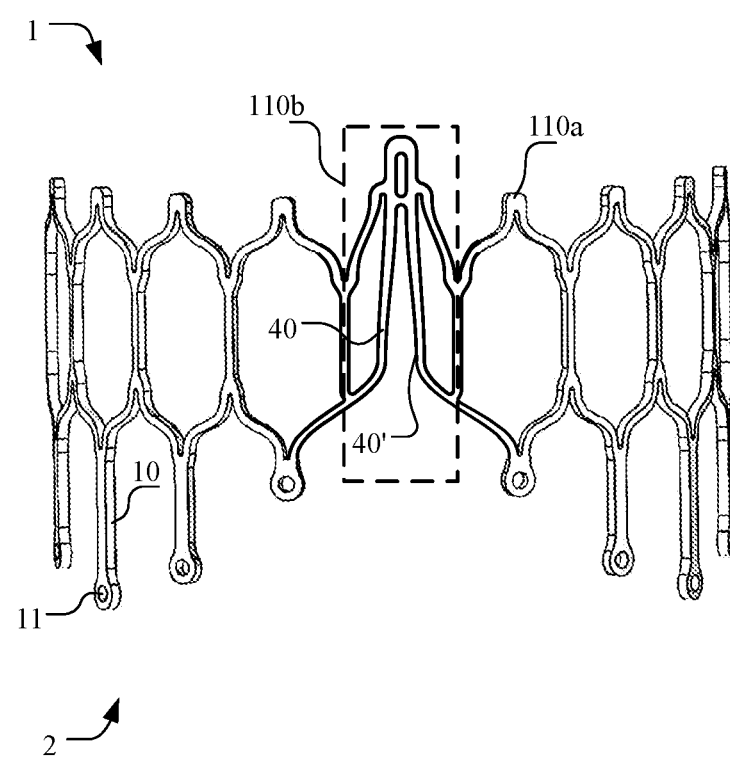
FIG. 19 shows a partial structural schematic diagram of a third exemplary structure of the stent according to an embodiment of the present disclosure.
Figure 20:
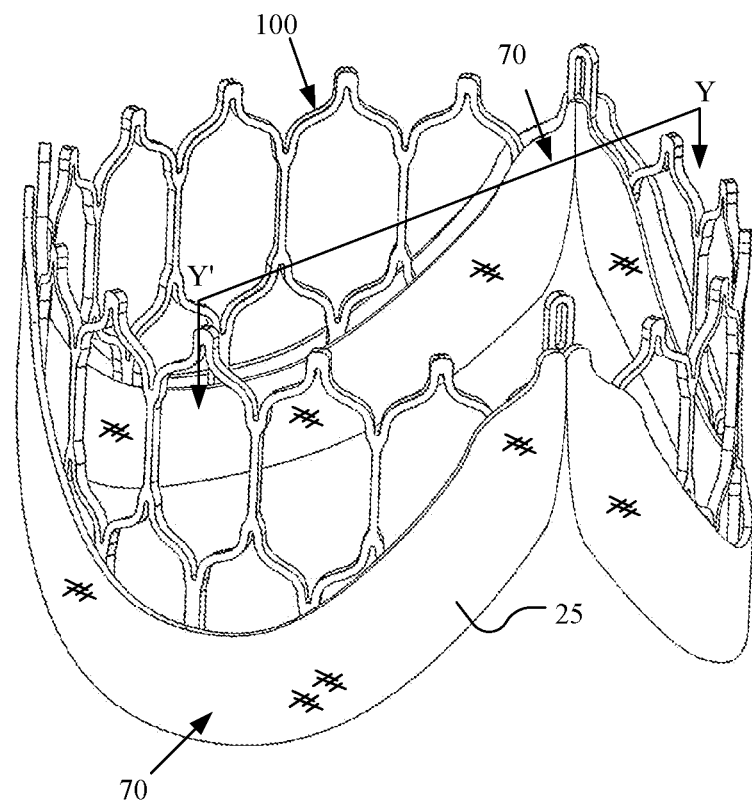
FIG. 20 shows a structural diagram of the stent shown in FIG. 19 with a third covering layer according to an embodiment of the present disclosure.
Figure 21:
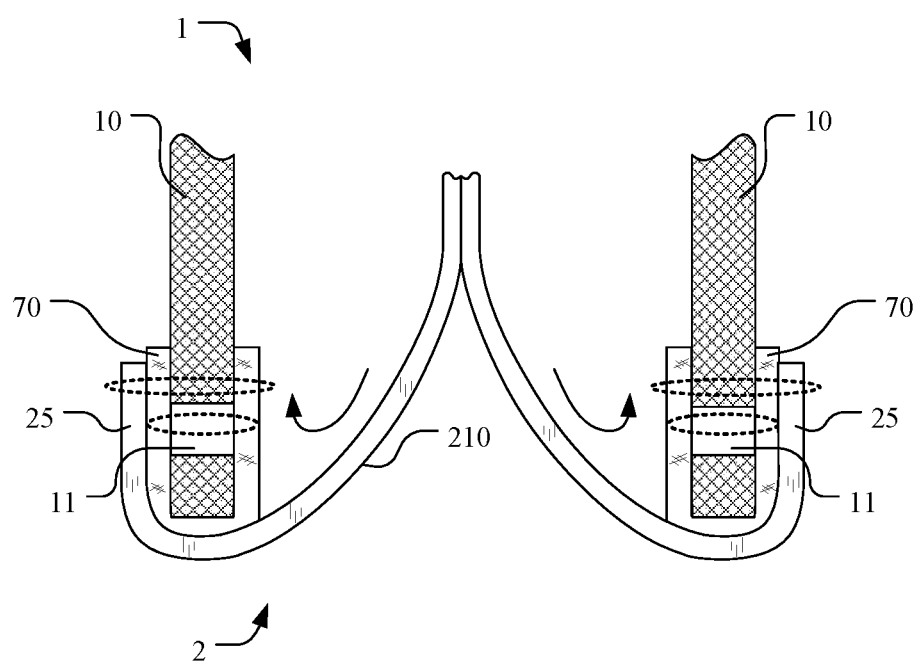
FIG. 21 shows a cross-section diagram of an implementation of the universal core along line YY' shown in FIG. 20.
Figure 22:
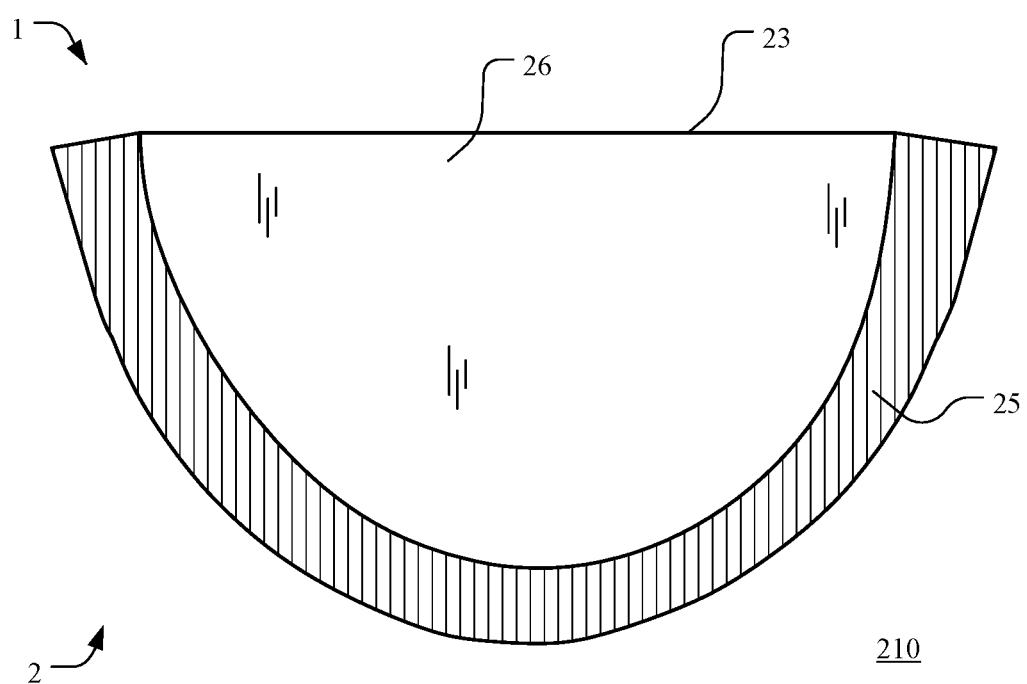
FIG. 22 shows a flattened view of a structure of a single leaflet according to an embodiment of the present disclosure.

FIG. 19 shows a partial structural schematic diagram of a third exemplary structure of the stent according to an embodiment of the present disclosure, FIG. 20 shows a structural diagram of the stent shown in FIG. 19 with a third covering layer according to an embodiment of the present disclosure, FIG. 21 shows a cross-section diagram of an implementation of the universal core along line YY' shown in FIG. 20, and FIG. 22 shows a flattened view of a structure of a single leaflet according to an embodiment of the present disclosure.

As shown in FIG. 19, in each second mesh cell 110b of the stent 100, the first edge 40 and the second edge 40' extend along the lower contour of the stent 100 to a position in contact with a top portion of that second mesh cell 110b at the distal end 1. As optional examples, a contacting point between the first edge 40 and the top portion of that second mesh cell 110b can be coincident with or separated from a contacting point between the second edge 40' and the top portion of that second mesh cell 110b, so that a gap used for receiving a continuous arcuate edge 25 (see FIG. 22) of a corresponding one of the plurality of leaflets 210 can be defined by the first edge and the second edge, thus each leaflet may have a continuous arcuate edge 25 which can be folded from the inner space of the stent 100 to the outer side of the stent 100 without forming a slit (such as the slit shown in FIG. 10), thus improving durability and material stability of the leaflet structure 200.

Specifically, as shown in FIG. 22, the continuous arcuate edge 25 of each leaflet 210 is formed by the side edges 21 and the lower edge 22 (referring to FIG. 10) that leaflet 210, and is folded to the outer side of the stent 100 based on the first connecting structure 82 and the plurality of cantilever struts 10, the first edge 40 of an adjacent one of the plurality of second mesh cells 110b and the second edge 40' of another adjacent one of the plurality of second mesh cells 110b. The continuous arcuate edge 25 of each leaflet is at least attached to a corresponding portion of the stent 100 at the proximal end 2.

Based on the stent structure according to FIG. 19, instead of providing the first covering layer and the second covering layer which are separated, a third covering layer 70 (as an example of the one-piece covering layer including the first covering layer and the second covering layer) can be provided as a base for stitching, in order to secure the leaflets 210 to the stent 100.

As shown in FIGS. 20, the third covering layer can be folded from the inner side of the stent 100 to the outer side of the stent 100 based on the first connecting structure 82 and the plurality of cantilever struts 10, and at least covers the first edges 40 and the second edges 40' of the plurality of second mesh cells 110b and the flexible ends of the plurality of struts 10 at the proximal end 2, so that at least a portion of an interval space between two adjacent ones of the plurality of cantilever struts 10 can be exposed.

Further, as shown in FIG. 21, the continuous arcuate edge 25 of each leaflet 210 can be secured with the third covering layer 70 by applying blanket, locking and/or other type of stitching through the third covering layer 70, thus can be attached to a corresponding portion of the stent 100 at the distal end 1 and/or the proximal end 2. The third covering layer 70 may be at least partially sandwiched between the continuous arcuate edge 25 and the corresponding portion of the stent 100 at the proximal end 2.

In some embodiments, taking FIG. 21 as an example, at least a portion, that is folded out from the interior of the stent 100 to an outer circumferential surface of the stent 100 based on the first connecting structure 82 and the plurality of cantilever struts 10, of the continuous arcuate edge 25 of each leaflet can be sewn along a certain distance (e.g., 5 mm) from an edge, at the proximal end 2 of the stent 100, to a position on the outer circumferential surface of the stent 100. In some optional embodiments, as the wrapped-over portion of each leaflet 210 is mainly for supporting that leaflet and improving the longevity of the prosthetic heart, sewing points for each leaflet can be positioned at the edge, at the proximal end 2 of the stent 100, all the way to an end, which is wrapped over to the outer circumferential surface of the stent 100, of the continuous arcuate edge 25.

In some optional embodiments, material of the third covering layer 70 can be PET or other material which promotes endothelialization. In some optional embodiments, thickness of the third covering layer 70 may be 0.05-0.5 mm, e.g., 0.1-0.25 mm.

Figure 23:
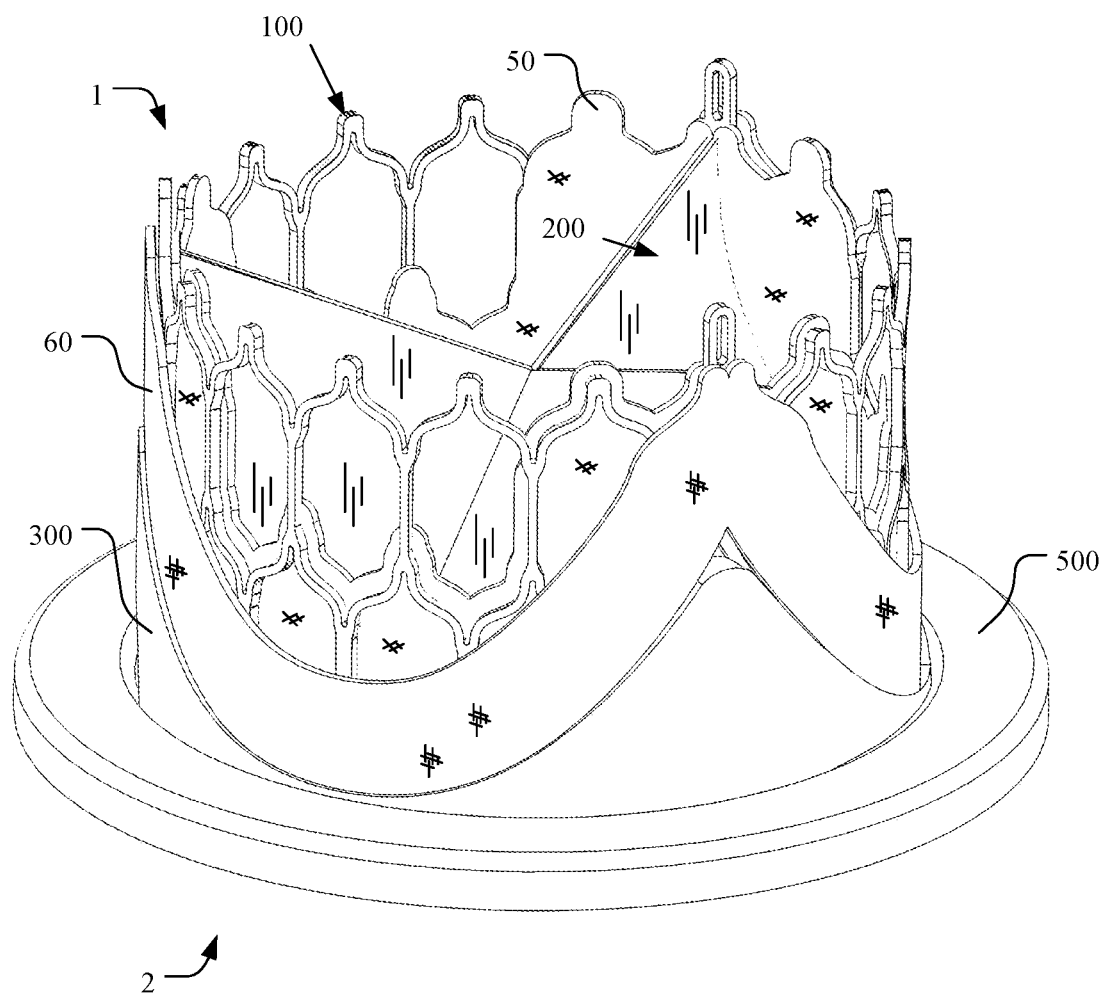
FIG. 23 shows a structural diagram of a prosthetic heart valve with a sewing ring according to an embodiment of the present disclosure.

FIG. 23 shows a structural diagram of a prosthetic heart valve with a sewing ring according to an embodiment of the present disclosure.

According to any one of the embodiments of the present disclosure, as shown in FIG. 23, a sewing ring 500 can be further provided. The sewing ring 500 is configured to matched with the designated adapter 300 and capable of being attached to an outer surface of the designated adapter 300 and the target implantation position.

In some optional embodiments, material of the sewing ring 500 can be PET or PTFE, etc.

Figure 24:
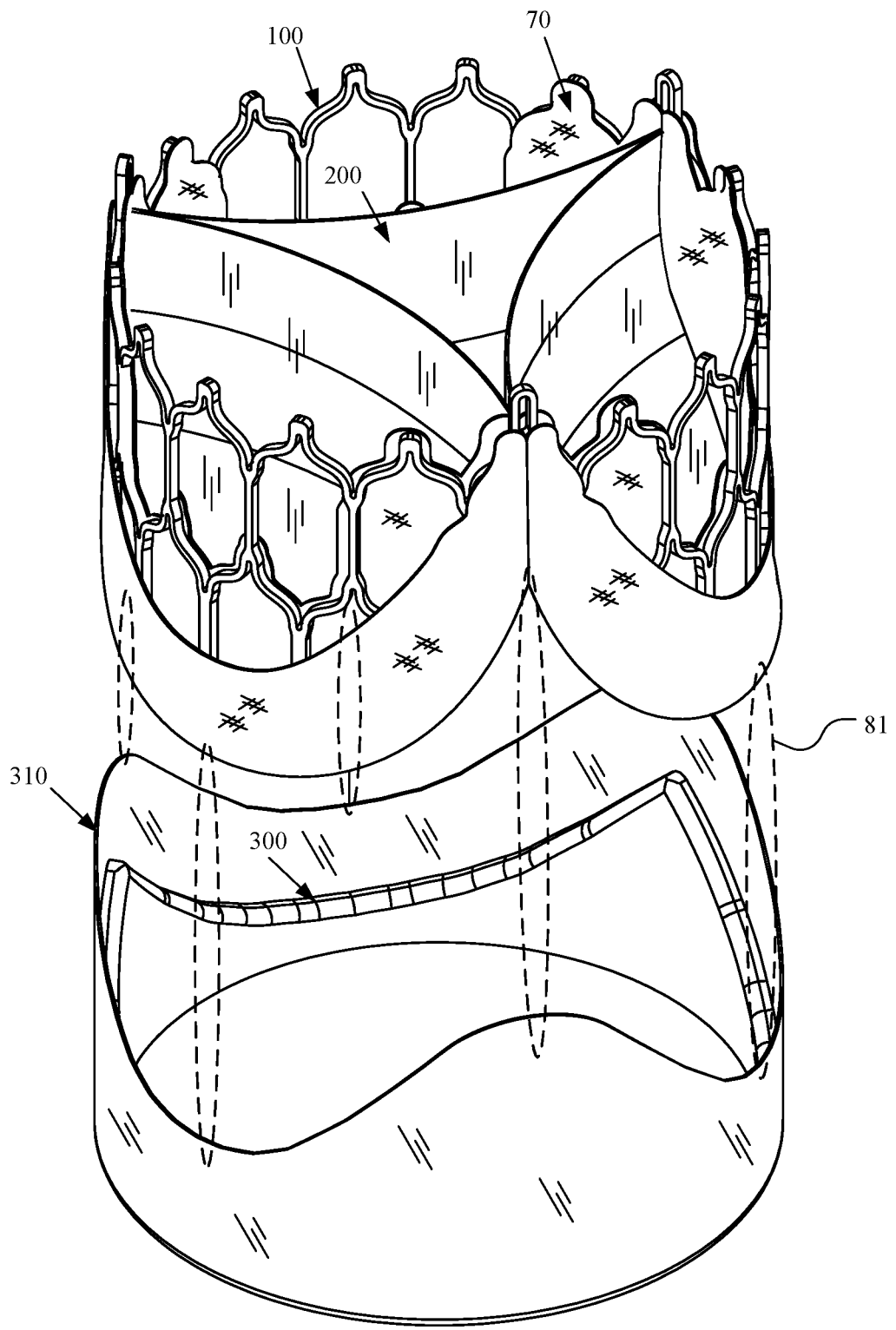
FIG. 24 shows a schematic structural diagram of a prosthetic heart valve with leaflets in open position open according to an embodiment of the present disclosure.
Figure 25:
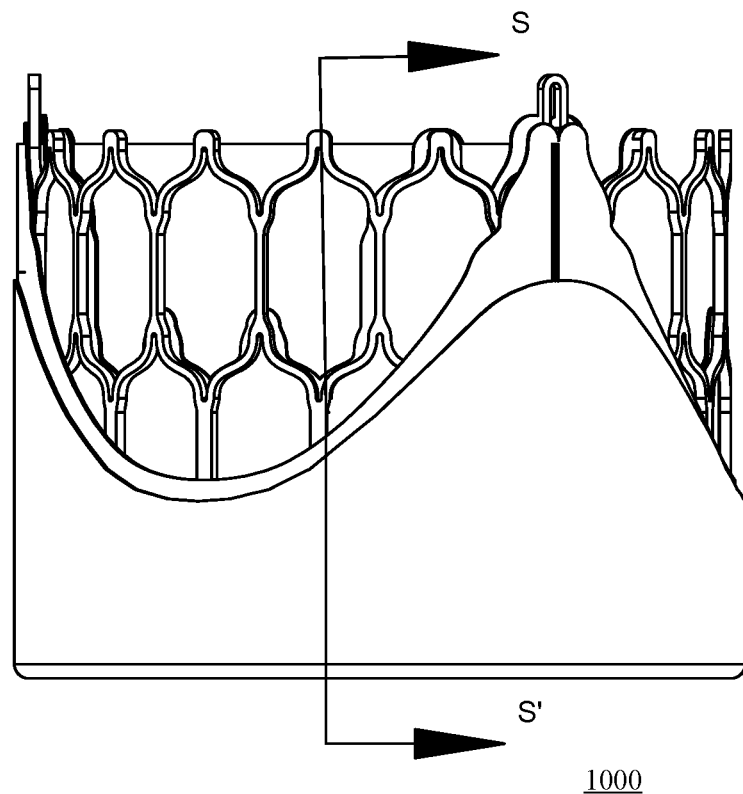
FIG. 25 shows a side view of a prosthetic heart valve with leaflets in open position according to an embodiment of the present disclosure.

FIG. 24 shows a schematic structural diagram of a prosthetic heart valve when the leaflets open according to an embodiment of the present disclosure; FIG. 25 shows a side view of a prosthetic heart valve with open-state leaflets according to an embodiment of the present disclosure, and FIG. 26 shows a cross-sectional diagram of the prosthetic heart valve with open-state leaflets along line SS' as shown in FIG. 25.

Figure 26:
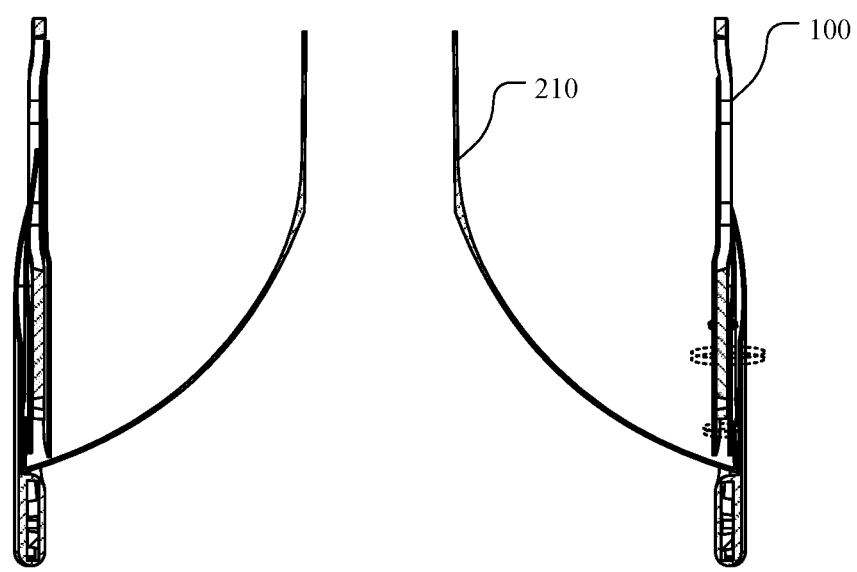
FIG. 26 shows a cross-sectional diagram of the prosthetic heart valve with leaflets in open position as shown in FIG. 25.

Referring to FIGS. 24 to 26, it should be noted that the leaflets 210 are configured to move between an open position to allow blood to flow through the prosthetic heart valve 1000 from the proximal end 2 to the distal end 1 and a closed position to inhibit the flow of blood through the prosthetic heart valve from the distal end 1 to the proximal end 2. FIG. 24 specifically illustrated the position and manner of attachments between the adapter 300 and stent 100.

In some embodiments, the prosthetic heart valve further comprises a base covering layer 310, which encloses an inner circumferential surface and/or an outer circumferential surface of the adapter 300, so as to prevent blood flow from flowing through a direction other than a direction between a proximal-end opening and a distal-end opening of the adapter 300.

In some embodiments, the base covering layer 310 may be sutured to one or both of the first covering layer 50 and the second covering layer 60.

In some optional embodiments, material of the base covering 310 may be polymer material, such as PET, so as to promote endothelialization.

In some optional embodiments, a thickness of the base covering 310 may be 0.05-0.5 mm, e.g., 0.1-0.25 mm.

According to embodiments of the present disclosure, an assembling method of the prosthetic heart valve in any embodiment of the present disclosure is provided, and mainly comprises following steps:

softly connecting the plurality of cantilever struts by the wire;

connecting each one of the plurality of leaflets together with the stent based on the wire and the plurality of cantilever struts by sewing; and selecting and connecting the designated adapter with the plurality of cantilever struts by sewing.

Detailed steps can be performed according to descriptions of embodiments of the prosthetic heart valve mentioned above, which will not be repeated here.

The prosthetic heart valve and the assembling method thereof provided according to the embodiments of the present disclosure is mainly a true 2-piece structure formed by a universal core and an adapter which are structurally and functionally independent with each other, and are detachably connected via cantilever struts of the universal core. The universal core comprises a leaflet structure and an annular stent with the cantilever struts and a mesh structure, and is universally suitable for various application scenarios, for example, allows for stand-alone surgical or clamp down transcatheter valve delivery. The stent with mesh structure provides stability for the prosthetic heart valve, and the leaflets are attached to the cantilever struts and/or a distal-end portion of the stent. According to a designated application scenario, the adapter can be selected from more than one adapters, which are respectively adapting to various application scenarios, and is configured to anchor the universal core at a corresponding implantation position. Each cantilever strut is a flexible cantilever that is configured to move in at least three degrees of freedom and allows for slight deformations from various adaptors of various applications, thus will have minimal impact on the valve structure. Therefore, the prosthetic heart valve provided according to the embodiments of the present disclosure has good universality and flexibility, and can obviously save cost of time, research, and development, improve the utilization efficiency of the production line, and accelerate the procedure to put the prosthetic heart valve in clinical practice and market.

Further, the plurality of cantilever struts can be softly connected by a wire, so as to form a supporting structure for the leaflet structure, and help improve the longevity of the prosthetic heart valve.

In some optional embodiments, the cantilever struts may be provided with cavities, a connecting structure (e.g., suture or wire) may pass through those cavities to form a support structure for supporting the leaflet structure, such that each leaflet may be attached to the stent at the proximal end based on the cantilever struts. Those cavities can also be used to be connected to the designated adapter.

In some optional embodiments, the second mesh cells can be provided with a strut/cavity to further provide steadily support for the commissures and/or edges of the leaflets.

In some optional embodiments, each second mesh cell can be provided with a gap for receiving a corresponding one of the leaflets, thus each leaflet may have a continuous arcuate edge which can be folded from the inner space of the stent to the outer side of the stent without forming a slit, thus improving durability and material stability of the leaflet structure.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim all that comes within the scope and spirit of these claims and their equivalents.

What is claimed is:

1. A prosthetic heart valve, comprising:
a universal core, adaptable for different application scenarios, comprised of
a ring-shaped stent, having a distal end and a proximal end in an axial direction, and comprising:
a mesh structure as a circumferential sidewall, which allows the stent to be contracted or expanded in a radial direction, wherein the stent is configured to have blood flow from the proximal end to the distal end; and
a plurality of cantilever struts, having various length, each of which extends distally from the proximal end of the mesh structure;
a leaflet structure comprising a plurality of leaflets, each of which is attached to the stent and at least has a portion disposed within the stent, wherein the leaflet structure allows blood to flow from the proximal end to the distal end through the prosthetic heart valve and inhibits blood flowing from the distal end to proximal end through the prosthetic heart valve;
a designated adapter, which is selected from more than one adapters suitable for the different application scenarios and configured to anchoring the stent at a target position, wherein the stent and any one of the more than one adapters are detachably connected with each other based on the plurality of cantilever struts,
wherein the plurality of cantilever struts, which are softly connected by a wire to form a supporting structure for the leaflet structure, are each configured to move in at least three degrees of freedom.

2. The prosthetic heart valve according to claim 1, wherein each one of the plurality of leaflets has an arc constraint edge for being secured with the sent, and a free edge which is disposed within the stent, wherein the free edge allows blood flowing from the proximal end to the distal end through the prosthetic heart valve when being separated from any other one of the plurality of leaflets, and inhibits blood flowing from the distal end to the proximal end through the prosthetic heart valve when being in contact with any other one of the plurality of leaflets,
wherein at least a portion of the arc constraint edge is folded out from an interior of the stent to an outer circumferential surface of the stent based on the wire and the plurality of cantilever struts, so as to make the arc constraint edge wrap over the wire and the proximal end of the stent.

3. The prosthetic heart valve according to claim 2, wherein the arc constraint edge of each one of the plurality of leaflets has a lower edge portion at the proximal end and opposing side edge portions, each of the edge portions is secured with an adjacent side edge portion of another one of the plurality of leaflets to form a commissure,
wherein the free edge extends between the side edge portions of the arc constraint edge, and the proximal end of the stent has a contour matched with a lower contour shaped by the lower edge portions of the plurality of leaflets.

4. The prosthetic heart valve according to claim 1, wherein the mesh structure comprises a plurality of first mesh cells and a plurality of second mesh cells distributed in a circumferential direction,
the plurality of leaflets are each attached to a corresponding one of the plurality of second mesh cells or a corresponding one of the plurality of cantilever struts, and are independent with the adapter.

5. The prosthetic heart valve according to claim 4, further comprising a first covering layer covering at least a portion of an inner side of the stent and having a skirt-like shape, wherein the first covering layer comprises:
a first portion, which is sutured with the plurality of second mesh cells, and is at least partially sandwiched between the plurality of leaflets and the plurality of second mesh cells; and/or
a second portion, which matches the proximal end of the stent in location and shape, and is sutured with a corresponding portion of the stent.

6. The prosthetic heart valve according to claim 5, wherein,
an edge, at the distal end, of the first covering layer has a contour matched with several frames of the mesh structure,
wherein the several frames comprise:
a distal-end frame of one or more of mesh cells comprising of the plurality of second mesh cells and the first mesh cells adjacent to each of the plurality of second mesh cells;
a proximal-end frame of one or more of the plurality of first mesh cells other than the first mesh cells adjacent to each of the plurality of second mesh cells;
a rod frame, which is shared by adjacent first mesh cells, of one or more of the first mesh cells adjacent to each of the plurality of second mesh cells.

7. The prosthetic heart valve according to claim 5, wherein,
the first covering layer at least fully covers the plurality of second mesh cells, a portion of the first mesh cells adjacent to each of the plurality of second mesh cells, and a portion of the plurality of cantilever struts, or
at least one of the plurality of first mesh cells is partially exposed by the first covering layer and at least a portion of an interval space between two adjacent ones of the plurality of struts are exposed by the first cover layer.

8. The prosthetic heart valve according to claim 5, further comprising a second covering layer covering an outer side of the stent and having a skirt-like shape, wherein the second covering layer comprises:
a first portion, which is sutured together with the plurality of second mesh cells and the first portion of the first covering layer; and/or
a second portion, which has a proximal-end contour matching the proximal end of the stent in location and shape, and is sutured together with a corresponding portion of the stent and the second portion of the first covering layer.

9. The prosthetic heart valve according to claim 8, wherein,
an edge, at the distal end, of the second covering layer has a contour matched with a distal-end frame of one or more of the plurality of second mesh cells.

10. The prosthetic heart valve according to claim 8, wherein,
the first covering layer and the second covering layer are integrated as a one-piece covering layer, which wraps over the proximal end of the stent based on the wire and the plurality of cantilever struts, and is at least partially sandwiched between the stent and the plurality of leaflets at the proximal end; or the first covering layer and the second covering layer are separated covering layers.

11. The prosthetic heart valve according to claim 8, further comprising a base covering layer, which encloses an inner circumferential surface and/or an outer circumferential surface of the adapter, so as to prevent blood flow from flowing through a direction other than a direction between a proximal-end opening and a distal-end opening of the adapter.

12. The prosthetic heart valve according to claim 11, wherein the base covering layer is sutured to one or both of the first covering layer and the second covering layer.

13. The prosthetic heart valve according to claim 2, wherein the at least a portion of the arc constraint edge of each one of the plurality of leaflets is sewn along a certain distance from an edge, at the proximal end of the stent, to a position on the outer circumferential surface of the stent.

14. The prosthetic heart valve according to claim 1, wherein,
the plurality of cantilever struts each have a cavity arranged at the proximal end, and the cavities of the plurality of cantilever struts are softly connected by the wire and are selected from holes, slots, and slits; and/or
material of the wire is metal or suture.

15. An assembling method of the prosthetic heart valve according to claim 1, comprising: softly connecting the plurality of cantilever struts by the wire;
connecting each one of the plurality of leaflets together with the stent based on the wire and the plurality of cantilever struts by sewing; and
selecting and connecting the designated adapter with the plurality of cantilever struts by sewing.

16. The assembling method according to claim 15, wherein each one of the plurality of leaflets has an arc constraint edge and a free edge which is disposed within the stent, the free edge allows blood flowing from the proximal end to the distal end through the prosthetic heart valve when being separated from any other one of the plurality of leaflets, and inhibits blood flowing from the distal end to the proximal end through the prosthetic heart valve when being in contact with any other one of the plurality of leaflets,
wherein step of connecting each one of the plurality of leaflets together with the stent based on the wire and the plurality of cantilever struts by sewing comprises:
folding at least a portion of the arc constraint edge of each one the plurality of leaflets out from an interior of the stent to an outer circumferential surface of the stent based on the wire and the plurality of cantilever struts, so as to make the arc constraint edge wrap over the wire and the proximal end of the stent; and
suturing the at least a portion of the arc constraint edge together with the proximal end of the stent.

17. The assembling method according to claim 16, wherein the mesh structure comprises a plurality of first mesh cells and a plurality of second mesh cells distributed in a circumferential direction,
the plurality of leaflets are each attached to a corresponding one of the plurality of second mesh cells and/or a corresponding one of the plurality of cantilever struts, and are independent with the adapter.

18. The assembling method according to claim 17, wherein the prosthetic heart valve further comprises a first covering layer covering at least a portion of an inner side of the stent and having a skirt-like shape, wherein the assembling method further comprises:
suturing a first portion of the first covering layer with the plurality of second mesh cells, so as to allow the first portion of the first covering layer being at least partially sandwiched between the plurality of leaflets and the plurality of second mesh cells; and/or
suturing a second portion of the first covering layer with a corresponding portion of the stent, wherein the second portion of the first covering layer matches the proximal end of the stent in location and shape.

19. The assembling method according to claim 18, wherein the prosthetic heart valve further comprises a second covering layer covering an outer side of the stent and having a skirt-like shape, wherein the assembling method further comprises:
suturing a first portion of the second covering layer together with the plurality of second mesh cells and the first portion of the first covering layer; and/or
suturing a second portion of the second covering layer together with a corresponding portion of the stent and the second portion of the first covering layer, wherein the second portion of the second covering layer matches the proximal end of the stent in location and shape.

20. The assembling method according to claim 19, further comprising:
providing a one-piece covering layer by laser cut as an integrated covering layer including the first covering layer and the second covering layer, wherein the one-piece covering layer wraps over the proximal end of the stent based on the wire and the plurality of cantilever struts, and is at least partially sandwiched between the stent and the plurality of leaflets at the proximal end; or
providing the first covering layer and the second covering layer which are separated.

21. The assembling method according to claim 19, wherein the prosthetic heart valve further comprises a base covering layer, which encloses an inner circumferential surface and/or an outer circumferential surface of the adapter, so as to prevent blood flow from flowing through a direction other than a direction between a proximal-end opening and a distal-end opening of the adapter.

22. The assembling method according to claim 21, further comprising: suturing the base covering layer to one or both of the first covering layer and the second covering layer.

23. The assembling method according to claim 16, wherein step of suturing the at least a portion of the arc constraint edge together with the proximal end of the stent comprises:
suturing the at least a portion of the arc constraint edge of each one of the plurality of leaflets by sewing along a certain distance from an edge, at the proximal end of the stent, to a position on the outer circumferential surface of the stent.

24. The assembling method according to claim 15, further comprising:
connecting a sewing ring to an outer surface of the designated adapter.

* * * * *